(12) United States Patent
Jenkins et al.

(10) Patent No.: US 11,773,448 B2
(45) Date of Patent: Oct. 3, 2023

(54) METHODS FOR ASSESSING RISK OF DEVELOPING COLORECTAL CANCER

(71) Applicant: The University of Melbourne, Parkville (AU)

(72) Inventors: Mark Jenkins, Parkville (AU); Daniel Buchanan, Parkville (AU); John L. Hopper, Parkville (AU)

(73) Assignee: THE UNIVERSITY OF MELBOURNE, Parkville (AU)

( * ) Notice: Subject to any disclaimer, the term of this patent is extended or adjusted under 35 U.S.C. 154(b) by 55 days.

(21) Appl. No.: 16/074,032

(22) PCT Filed: Jan. 27, 2017

(86) PCT No.: PCT/AU2017/050066
§ 371 (c)(1),
(2) Date: Jul. 30, 2018

(87) PCT Pub. No.: WO2017/127893
PCT Pub. Date: Aug. 3, 2017

(65) Prior Publication Data
US 2019/0161802 A1    May 30, 2019

(30) Foreign Application Priority Data

Jan. 28, 2016 (AU) ................. 2016900254
Aug. 16, 2016 (AU) ................. 2016903246

(51) Int. Cl.
*C12Q 1/6886* (2018.01)
*G16B 20/20* (2019.01)
*C40B 40/06* (2006.01)

(52) U.S. Cl.
CPC ............ *C12Q 1/6886* (2013.01); *C40B 40/06* (2013.01); *G16B 20/20* (2019.02); *C12Q 2600/156* (2013.01)

(58) Field of Classification Search
None
See application file for complete search history.

(56) References Cited

U.S. PATENT DOCUMENTS

| | | |
|---|---|---|
| 6,174,170 B1 | 1/2001 | Wittwer |
| 6,897,025 B2 | 5/2005 | Cox |
| 6,898,531 B2 | 5/2005 | Sheehan |
| 6,969,589 B2 | 11/2005 | Patil |
| 7,127,355 B2 | 10/2006 | Cox |
| 2003/0108919 A1 | 6/2003 | Kautzer |
| 2004/0023237 A1 | 2/2004 | Patil |
| 2004/0241657 A1 | 12/2004 | Patil |
| 2005/0019787 A1 | 1/2005 | Berne |
| 2016/0102358 A1* | 4/2016 | Xu ............. C12Q 1/6886 506/2 |

FOREIGN PATENT DOCUMENTS

| | | |
|---|---|---|
| WO | WO 92/02638 A1 | 2/1992 |
| WO | WO 2016/061246 A1 | 4/2016 |

OTHER PUBLICATIONS

Nissen et al. Breast and colorectal cancer survivor's knowledge about their diagnosis and treatment. J Cancer Surviv 2012, 6, 20-32 (Year: 2012).*
Van Blarigan et al. Role of Physical Activity and Diet After colorectal Cancer Diganosis. J Clin Oncol 2015, 33: 1825-1834 (Year: 2015).*
Ricchi et al. Nonsteroidal anti-inflammatory drugs in colorectal cancer: from prevention to therapy. British Journal of Cancer 2003, 88, 803-807 (Year: 2003).*
Drew et al. Aspiring and colorectal cancer: the promise of precision chemoprevention. Nature Reviews Cancer Mar. 2016, vol. 16, pp. 173-186 (Year: 2016).*
Teixeira et al. Primary prevention fo colorectal cancer: Myth or reality? World J Gastroenterol 2014, 20(41), pp. 15060-15069 (Year: 2014).*
Komiya et al. Prevention and Intervention Trials for Colorectal Cancer. Jpn J Clin Oncol 2013, 43(7), pp. 685-694 (Year: 2013).*
International Search Report dated Mar. 10, 2017 in connection with PCT International Application No. PCT/AU2017/050066.
Written Opinion of the International Searching Authority dated Mar. 10, 2017 in connection with PCT International Application No. PCT/AU2017/050066.
Hsu, L. et al., "A Model to Determine Colorectal Cancer Risk Using Common Genetic Susceptibility Loci", *Gastroenterology*, Jun. 2015, 148(7): 1330-1339.
Al-Tassan, N. et al., "A new GWAS and meta-analysis with 1000Genomes imputation identifies novel risk variants for colorectal cancer", *Scientific Reports*, 2015, 5:10442.
Cheng, T.H.T. et al., "Meta-analysis of genome-wide association studies identifies common susceptibility polymorphisms for colorectal and endometrial cancer near SH2B3 and TSHZ1", *Scientific Reports*, 2015, 5:17369.
Dunlop et al., "Common variation near CDKN1A, POLD3, and SHROOM2 influences colorectal cancer risk" *Nat Genet.*, Feb. 2016; 44(7), 770-776.
Jenkins, M.A. et al., "Quantifying the utility of single nucleotide polymorphisms to guide colorectal cancer screening" *Future Oncology*, 2016, 12(4), 503-513.
Ait Oukraim, D. et al. "Screening practices of unaffected people at familial risk of colorectal cancer", Cancer Prev. Res. (Phila.), 5(2): 240-247 (Feb. 2012).
Antoniou, A.C. and Easton, D.F. "Polygenic Inheritance of Breast Cancer: Implications for Design of Association Studies", Genetic Epidemiology, 25:190-202 (2003).

(Continued)

*Primary Examiner* — Olivia M. Wise
(74) *Attorney, Agent, or Firm* — Gary J. Gershik

(57) ABSTRACT

Methods and systems for assessing the risk of a human subject for developing colorectal cancer are provided. These methods may be combined with the subject's clinical risk to improve risk analysis. Such methods may be used to assist decision making about appropriate colorectal cancer screening regimens.

Figure 1:
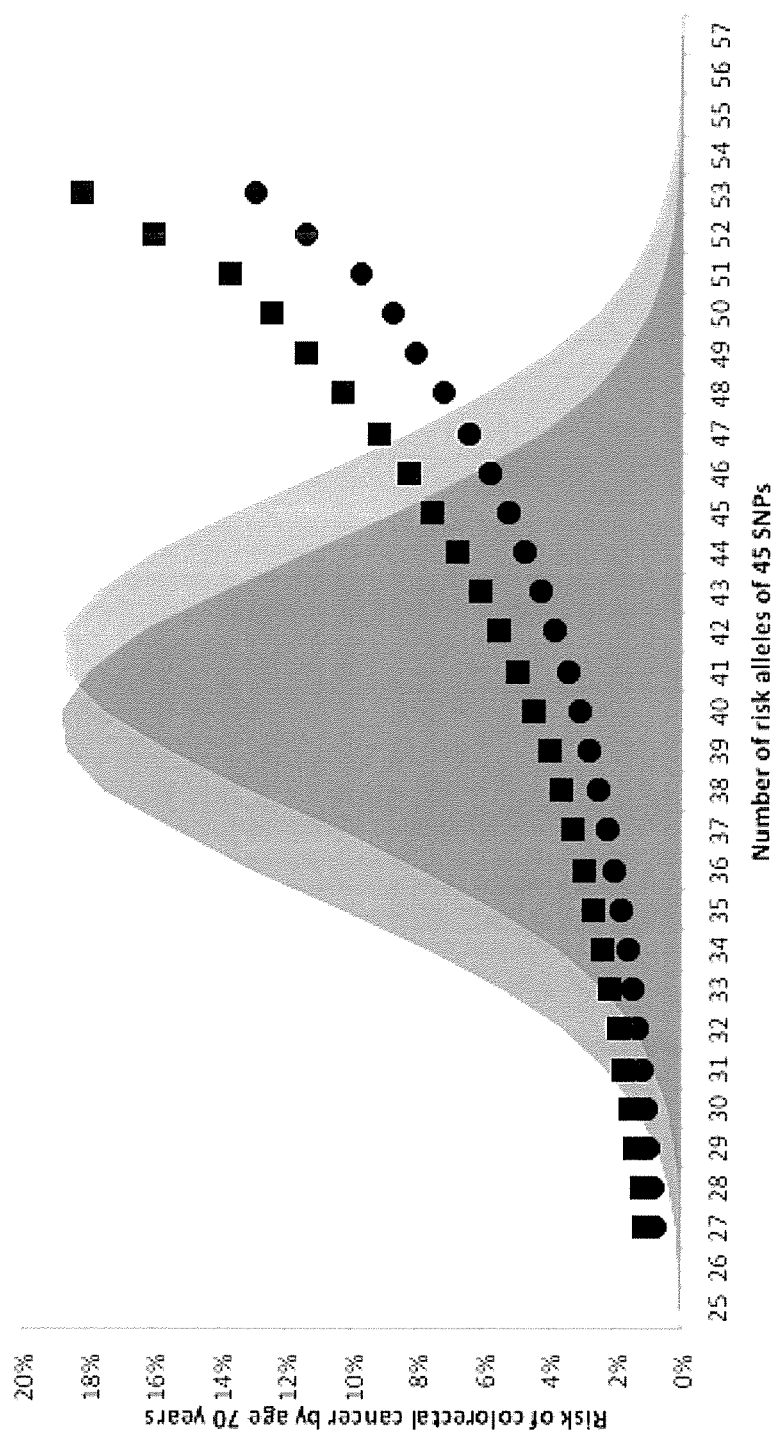
Figure 2A:
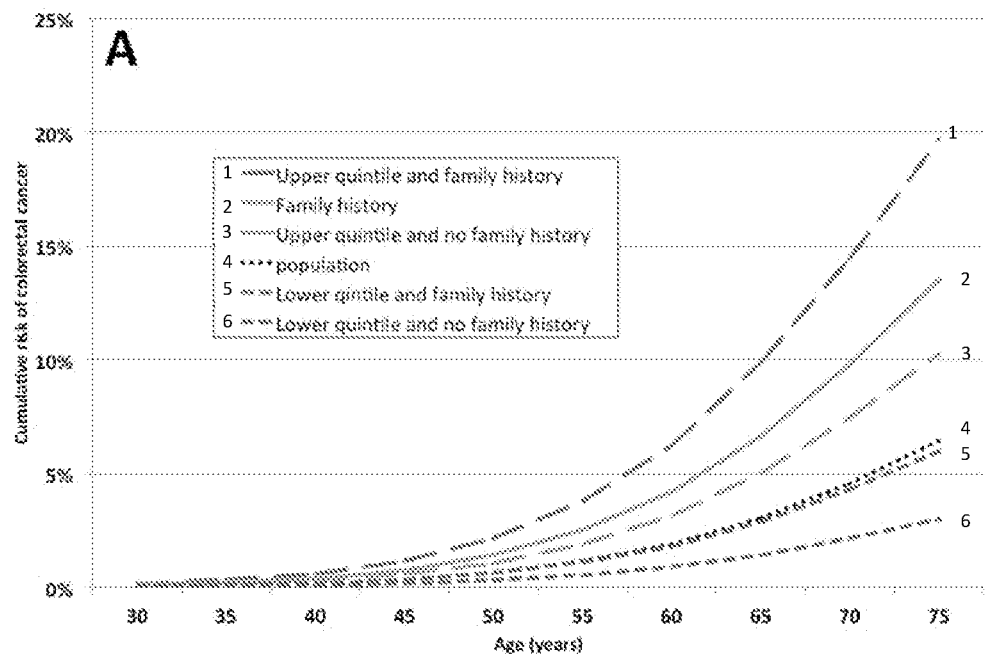
Figure 2B:
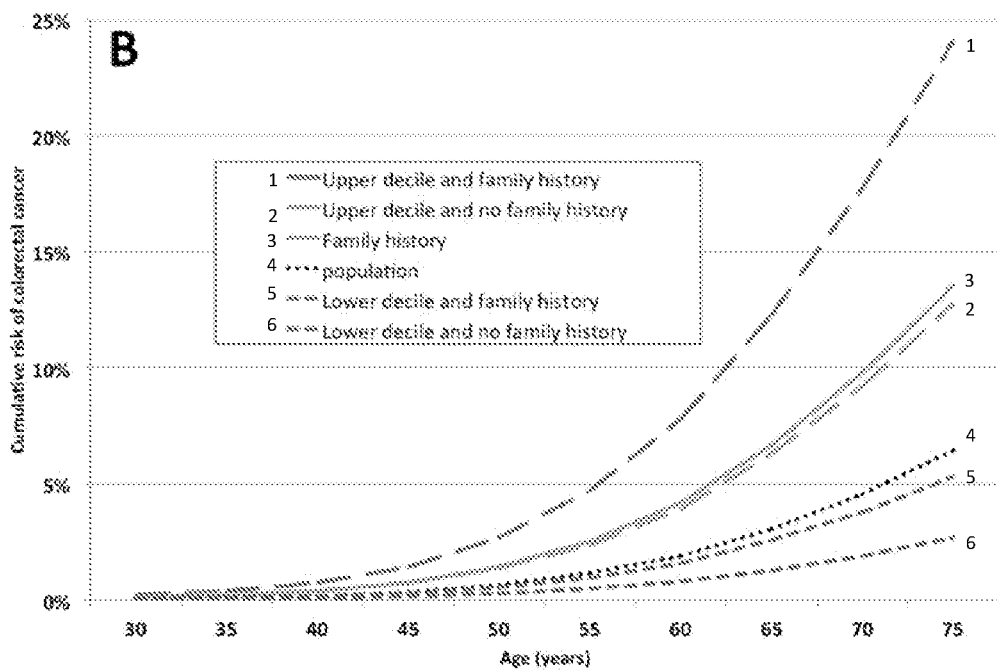
Figure 2C:
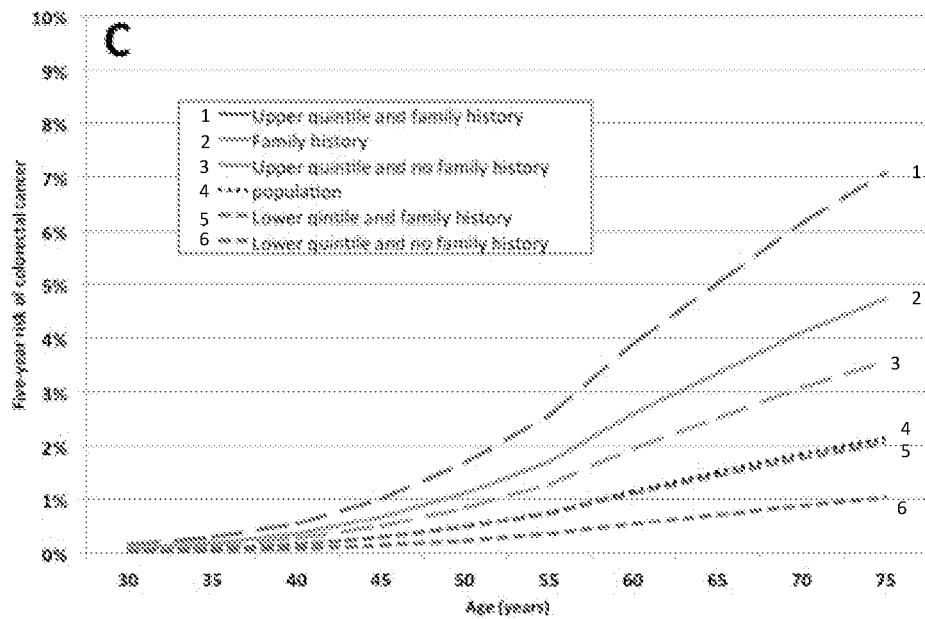
Figure 2D:
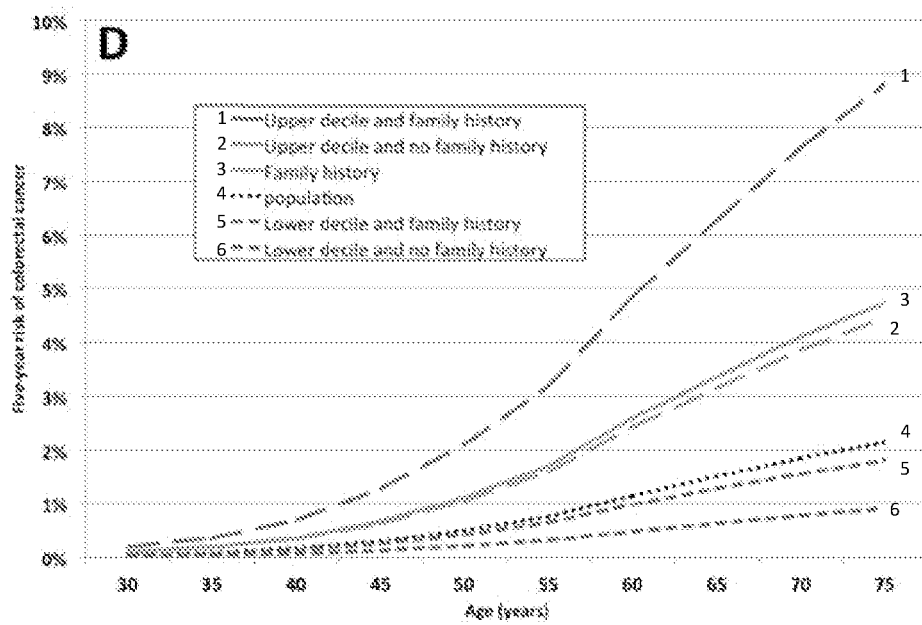
Figure 3A:
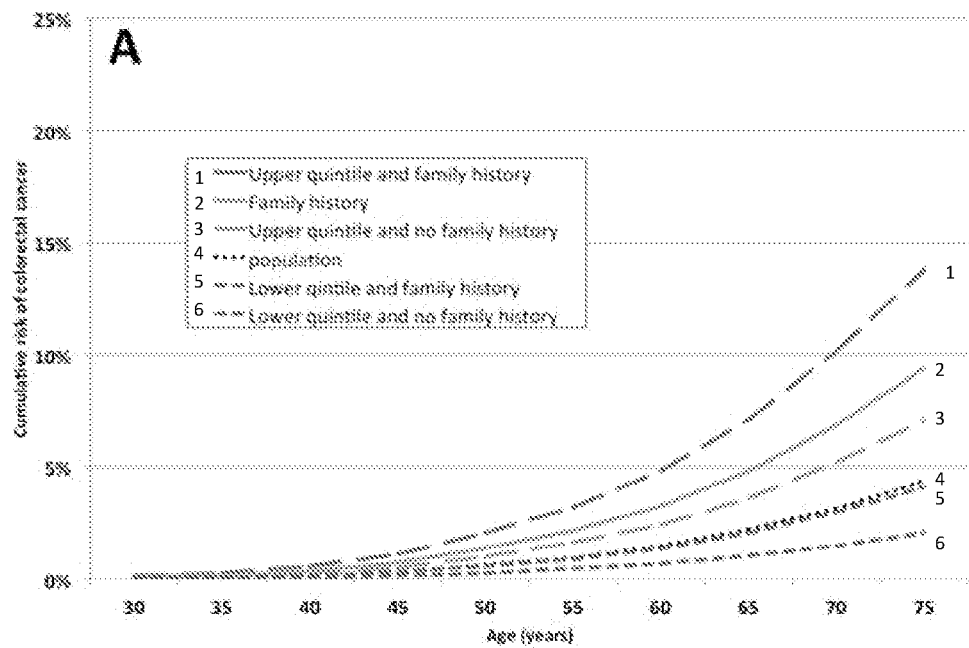
Figure 3B:
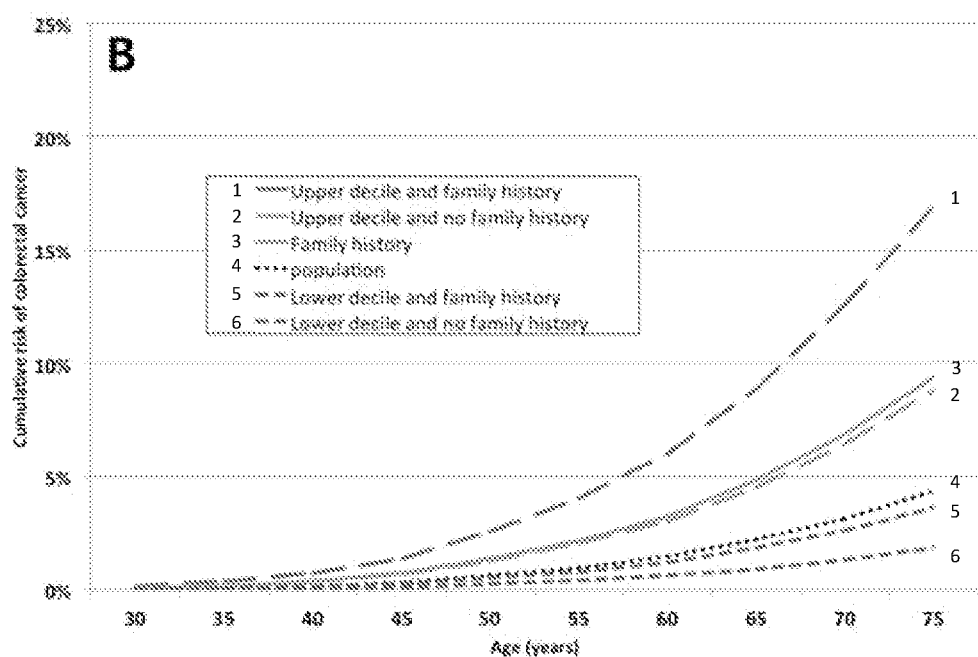
Figure 3C:
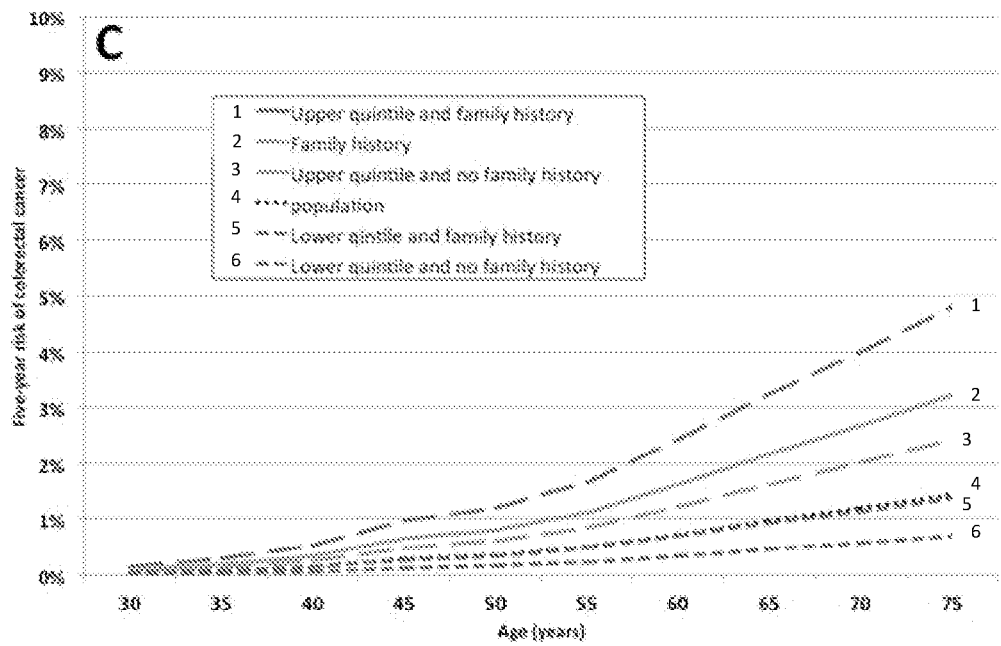
Figure 3D:
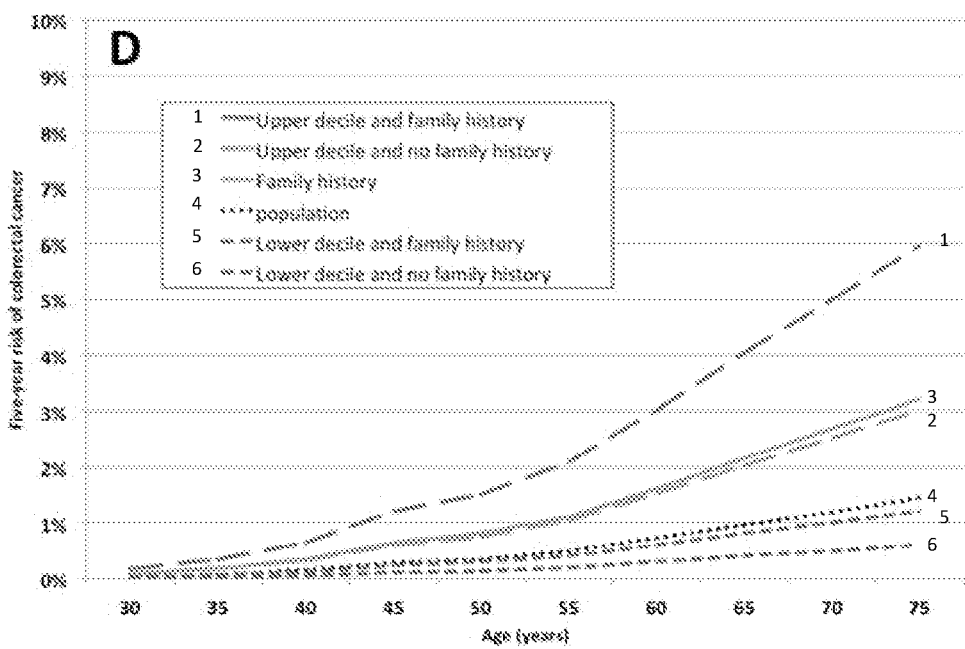
Figure 4A:
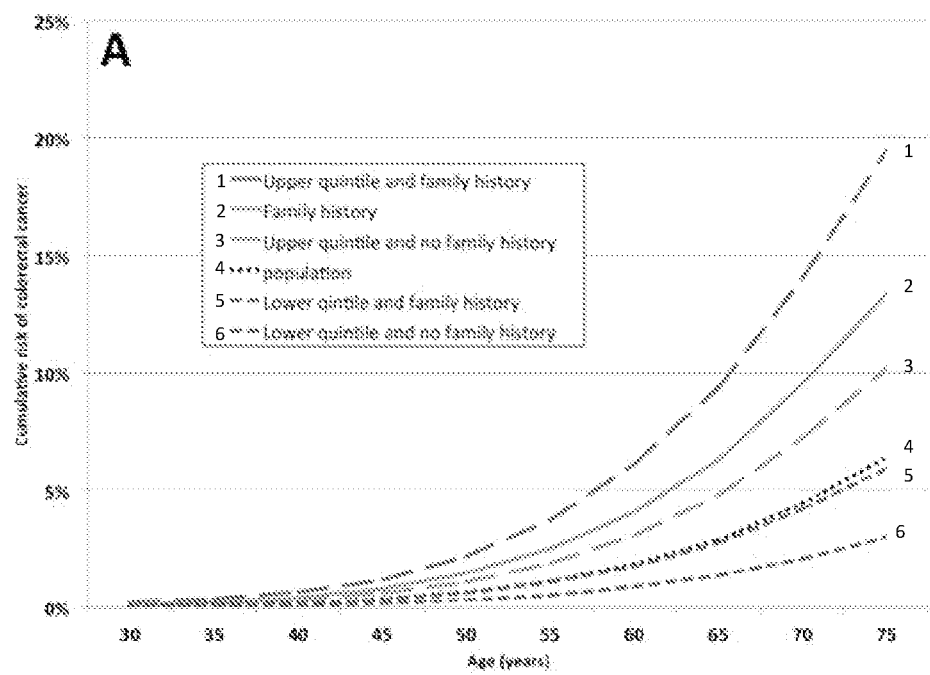
Figure 4B:
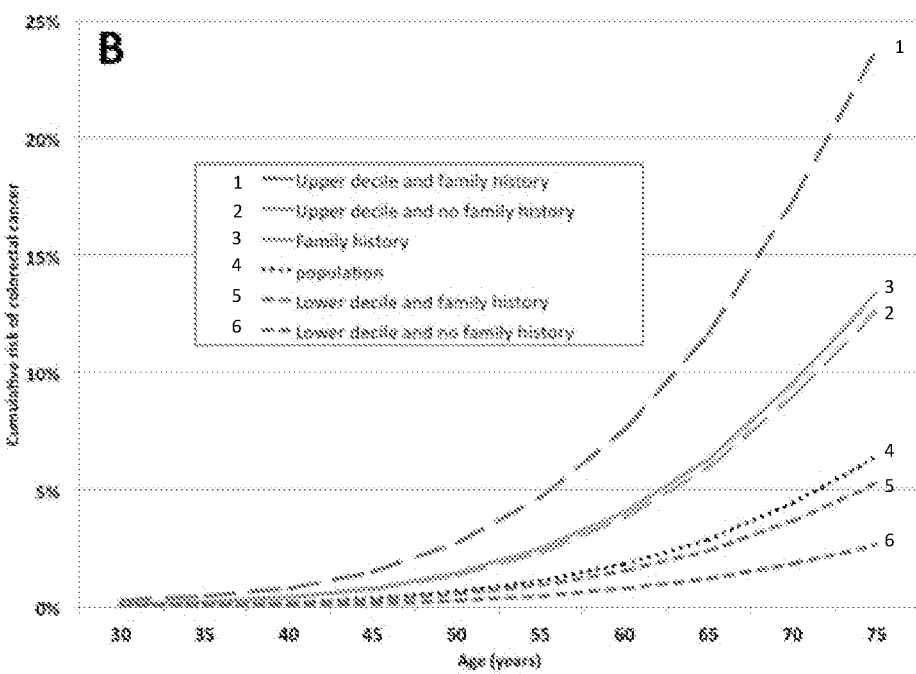
Figure 4C:
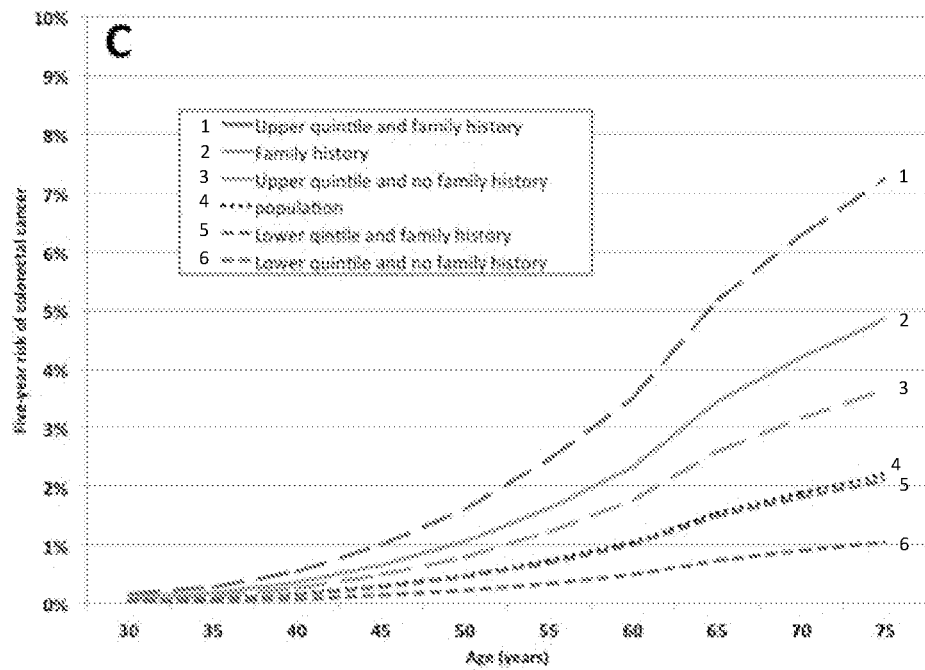
Figure 4D:
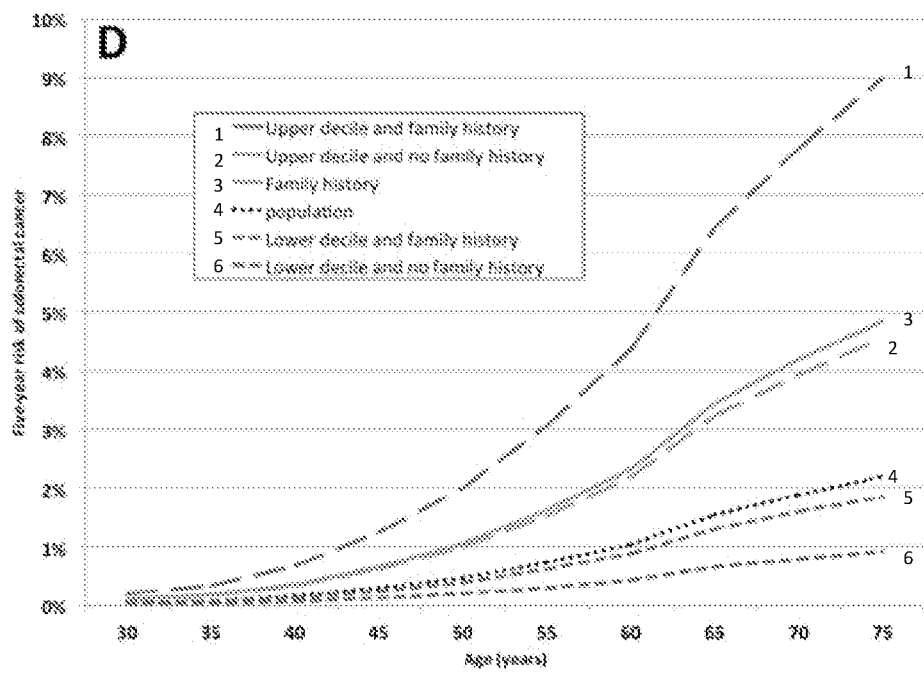
Figure 5A:
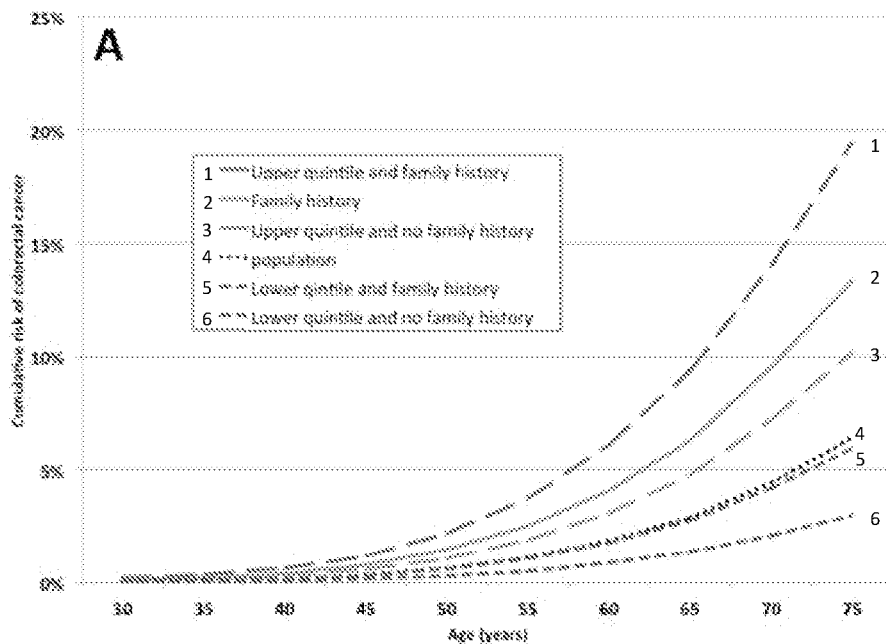
Figure 5B:
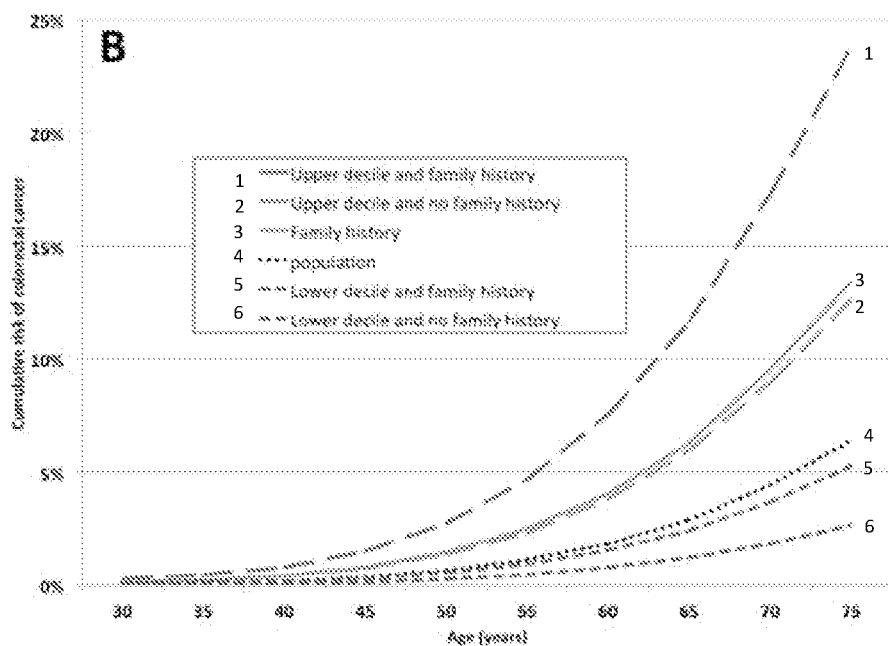
Figure 5C:
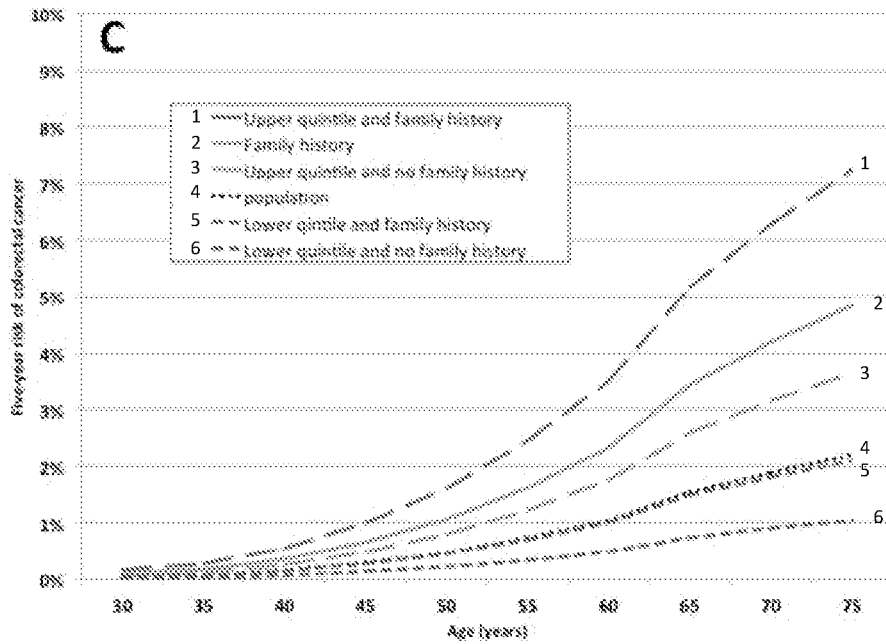
Figure 5D:
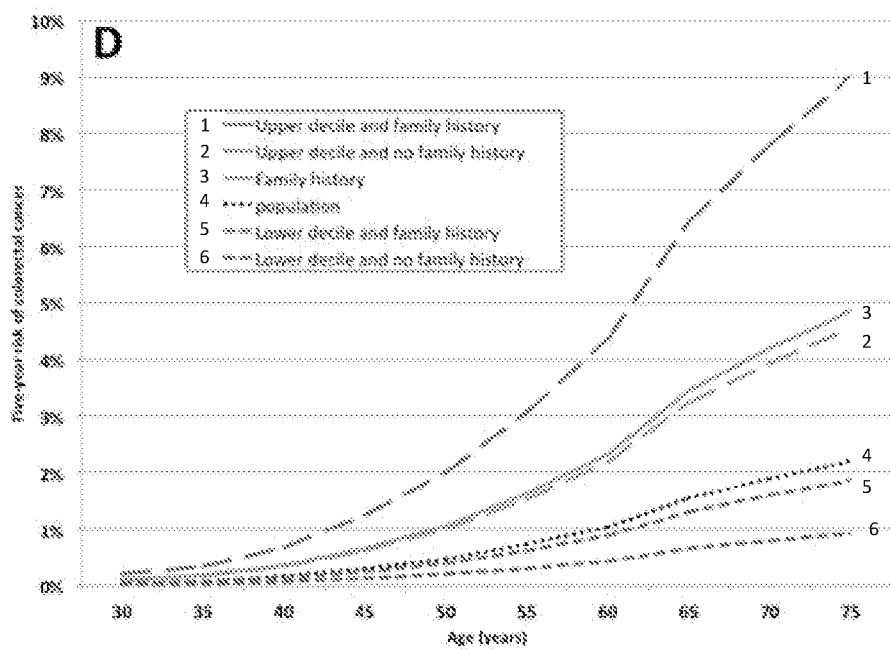
Figure 6A:
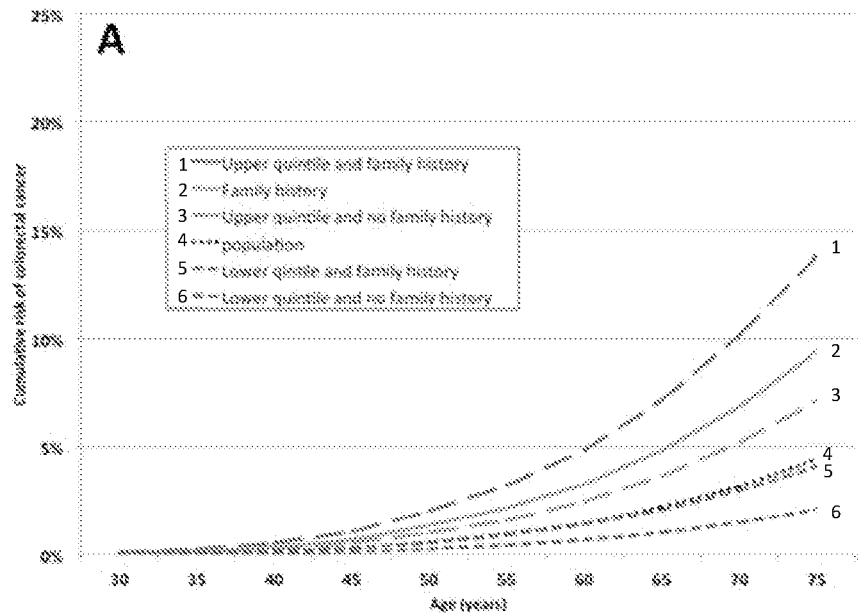
Figure 6B:
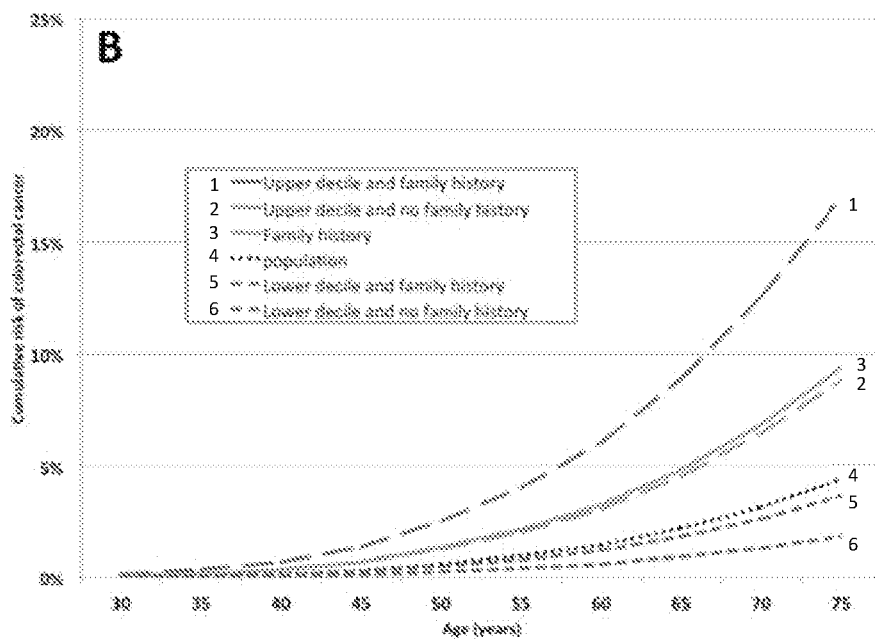
Figure 6C:
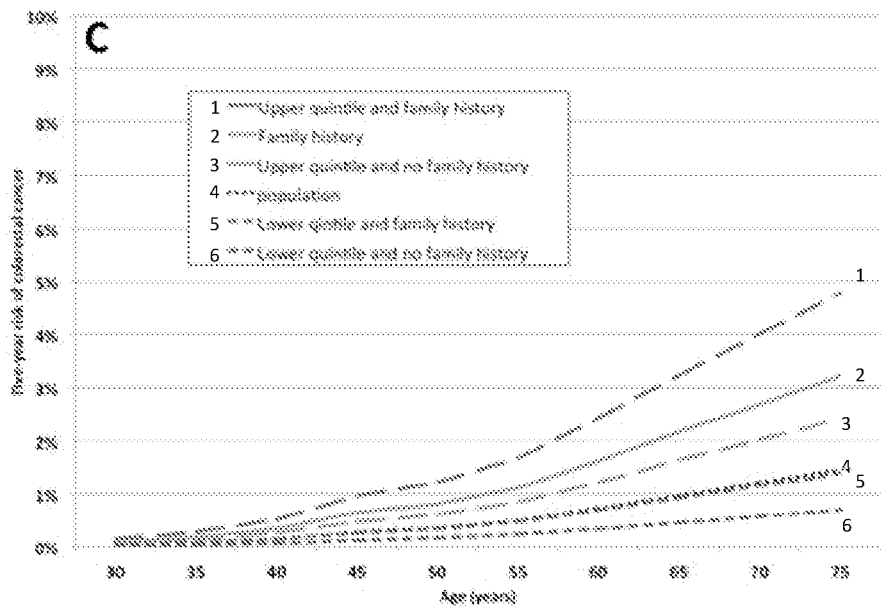
Figure 6D:
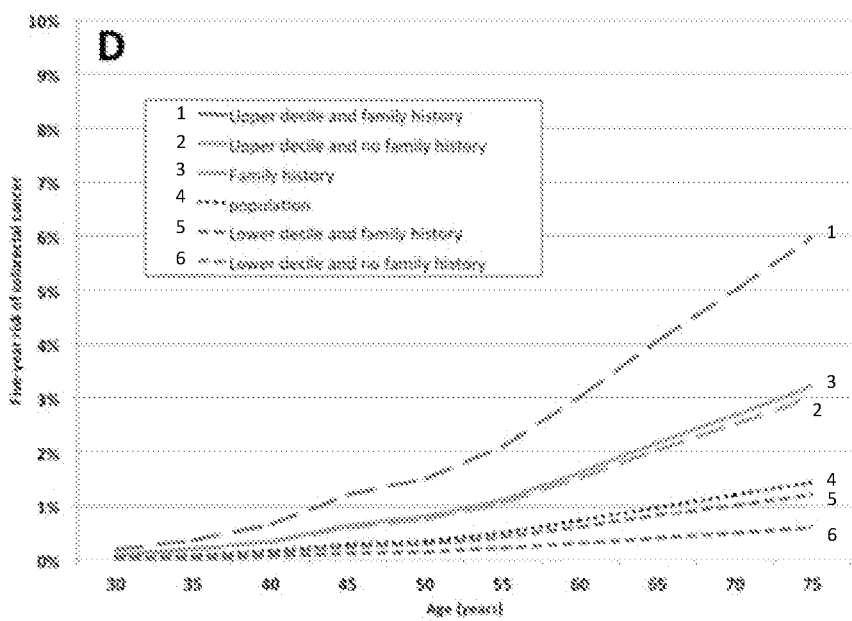
Figure 7A:
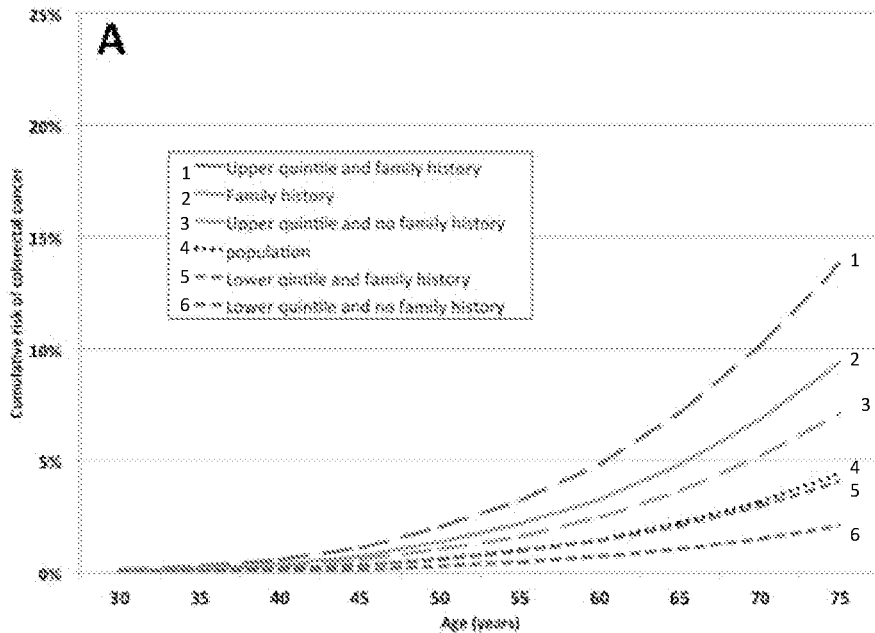
Figure 7B:
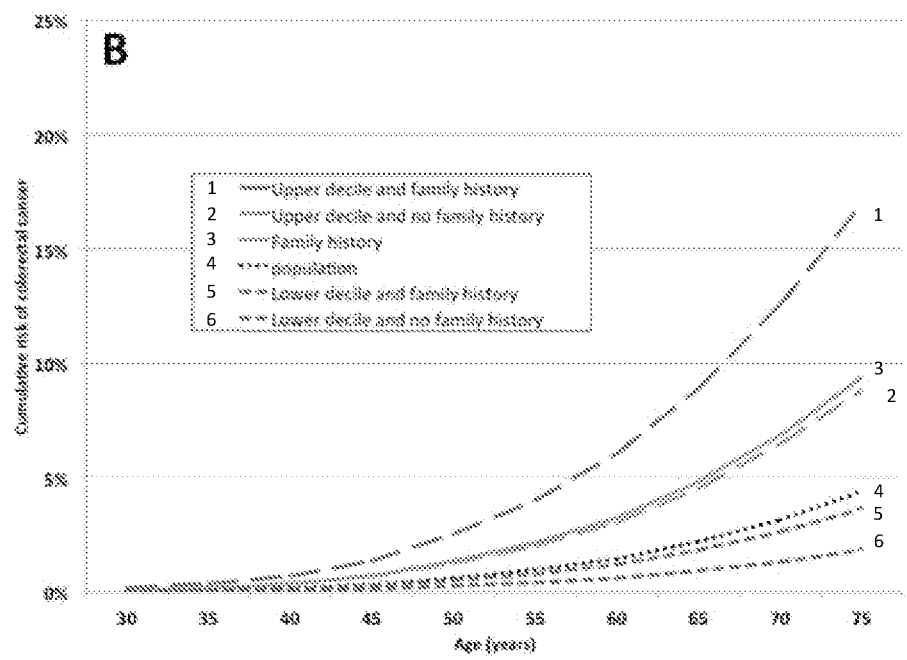
Figure 7C:
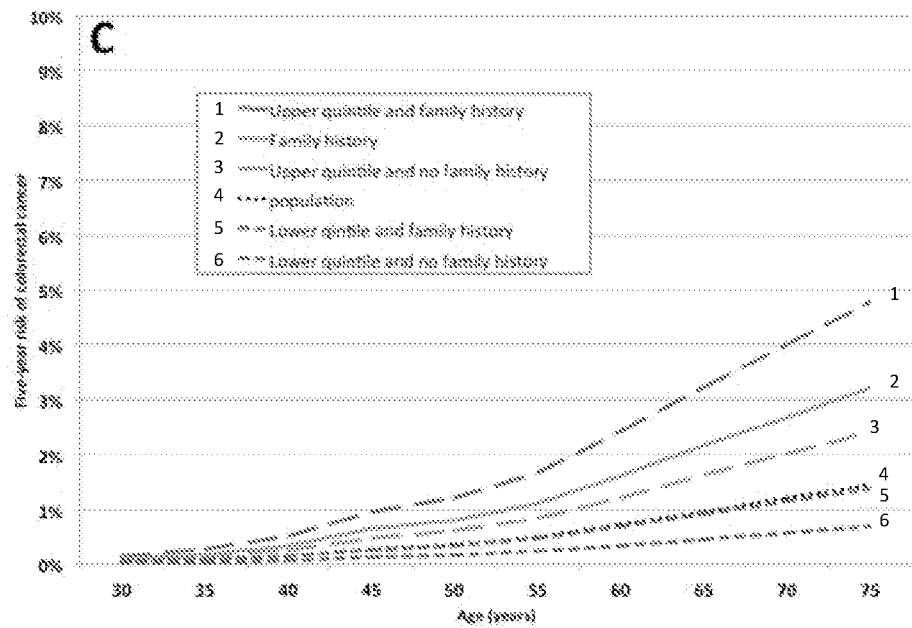
Figure 7D:
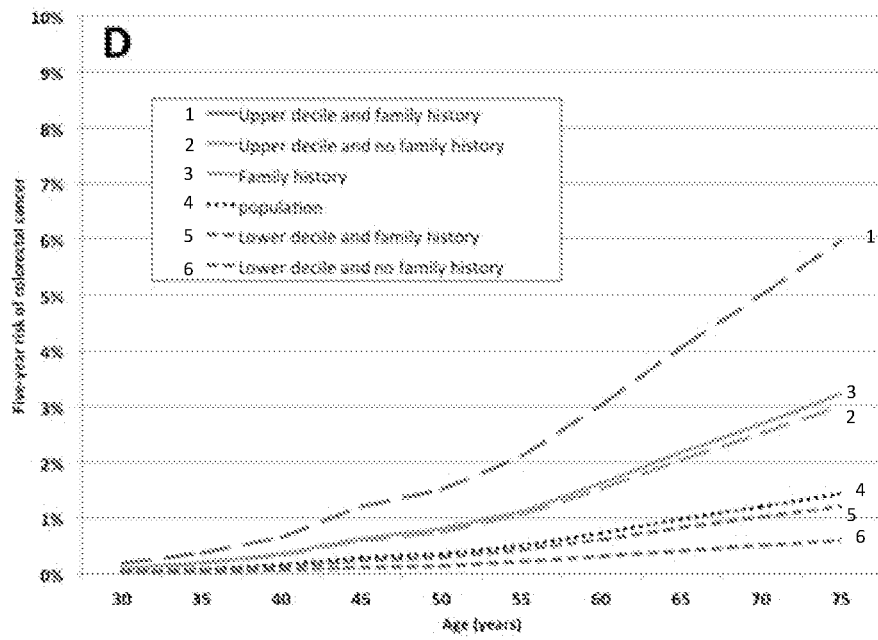

16 Claims, 13 Drawing Sheets
Specification includes a Sequence Listing.

(56) References Cited

OTHER PUBLICATIONS

Brenner, H. et al. "Effect of screening sigmoidoscopy and screening colonoscopy on colorectal cancer incidence and mortality: systematic review and meta-analysis of randomised controlled trials and observational studies", BMJ, 348:g2467, doi: 10.1136/bmj.g2467 (2014).
Ryan, B.M. et al. "An analysis of genetic factors related to risk of inflammatory bowel disease and colon cancer", Cancer Epidemiology, 38: 583-590 (2014).
Chee, M. et al. "Accessing Genetic Information with High-Density DNA Arrays", Science, 274: 610-614 (Oct. 25, 1996).
Devlin, B. and Risch, N. "A Comparison of Linkage Disequilibrium Measures for Fine-Scale Mapping", Genomics, 29: 311-332 (1995).
Dite, G.S. et al. "Breast Cancer Risk Prediction Using Clinical Models and 77 Independent Risk-Associated SNPs for Women Aged Under 50 Years: Australian Breast Cancer Family Registry", Cancer Epidemiol. Biomarkers Prev., 25(2): 359-365 (Feb. 2016).
Fodor, S.P.A. "Massively Parallel Genomics", Science, 277: 393-401 (Jul. 18, 1997).
Hewitson, P. et al. "Screening for colorectal cancer using the faecal occult blood test, Hemoccult", Cochrane Database Syst. Rev., 1 (CD001216): 1-31 (2011).
Johns, L.E. and Houlston, R.S. "A Systematic Review and Meta-Analysis of Familial Colorectal Cancer Risk", Am. J. Gastroenterology, 96(10): 2992-3003 (2001).
Lockhart, D.J. "Mutant yeast on drugs", Nature Medicine, 4(11): 1235-1236 (Nov. 1998).
Mavaddat, N. et al. "Prediction of Breast Cancer Risk Based on Profiling With Common Genetic Variants", J. Nat'l. Cancer Inst., 107(5): doi:10.1093/jnci/djv036 (Apr. 2, 2015).
Pencina, M. et al. "Evaluating the added predictive ability of a new marker: From area under the ROC curve to reclassification and beyond", Statist. Med. 27:157-172 (2008).
Purcell, S. et al. "PLINK: A Tool Set for Whole-Genome Association and Population-Based Linkage Analyses", Am. J. Human Genetics, 81: 559-575 (Sep. 2007).
Real, L.M. et al. "A Colorectal Cancer Susceptibility New Variant at 4q26 in the Spanish Population Identified by Genome-Wide Association Analysis", Plos One, 9(6): e101178 (Jun. 2014).
Sapolsky, R.J. et al. "High-throughput polymorphism screening and genotyping with high-density oligonucleotide arrays", Genetic Analysis: Biomolecular Engineering, 14: 187-192 (1999).
Schmit, S.L. et al. "A novel colorectal cancer risk locus at 4q32.2 identified from an international genome-wide study", Carcinogenesis, 35 (11): 2512-2519 (2014).
Slatkin, M. and Excoffier, L. "Testing for linkage disequilibrium in genotypic data using the Expectation-Maximization algorithm", Heredity, 76: 377-383 (1996).
Spain, S.L. et al. "Refinement of the associations between risk of colorectal cancer and polymorphisms on chromosomes 1q41 and 12q13.13", Human Mol. Genet., 21 (4): 934-946 (2012).
Usher-Smith, J.A. et al. "Risk Prediction Models for Colorectal Cancer: A Systematic Review", Cancer Prev. Res. 9(1): 13-26 (Jan. 2016).
Win, et al. "Risk of Colorectal Cancer for Carriers of Mutations in MUTYH, With and Without a Family History of Cancer", Gastroenterology, 146: 1208-1211 (2014).
Jul. 31, 2018 International Preliminary Report on Patentability issued in connection with corresponding PCT International Application No. PCT/AU2017/050066.
Dec. 12, 2019 Extended European Search Report issued in connection with corresponding European Patent Application No. 17743495.8.

* cited by examiner

SEQUENCE LISTING

<160> NUMBER OF SEQ ID NOS: 12

<210> SEQ ID NO 1
<211> LENGTH: 19
<212> TYPE: DNA

```
<213> ORGANISM: Artificial Sequence
<220> FEATURE:
<223> OTHER INFORMATION: Synthetic primer sequence

<400> SEQUENCE: 1
tgcagcaagt ggtgagaag                                                    19

<210> SEQ ID NO 2
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 2
cccattgtta ccagtatgaa gagt                                              24

<210> SEQ ID NO 3
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 3
agacactctc ctctgttgat tt                                                22

<210> SEQ ID NO 4
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 4
ggacatcaaa taatgtgcct agaa                                              24

<210> SEQ ID NO 5
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 5
cctgagtagc tgggactaca                                                   20

<210> SEQ ID NO 6
<211> LENGTH: 19
<212> TYPE: DNA
<213> ORGANISM: Artificial Sequence
<220> FEATURE:
<223> OTHER INFORMATION: Synthetic primer sequence

<400> SEQUENCE: 6
tcgagaccat cctggctaa                                                    19

<210> SEQ ID NO 7
<211> LENGTH: 18
<212> TYPE: DNA
<213> ORGANISM: Artificial Sequence
<220> FEATURE:
<223> OTHER INFORMATION: Synthetic primer sequence

<400> SEQUENCE: 7
aacggtcaga cgcaaaca                                                     18
```

```
<210> SEQ ID NO 8
<211> LENGTH: 23
<212> TYPE: DNA
<213> ORGANISM: Artificial Sequence
<220> FEATURE:
<223> OTHER INFORMATION: Synthetic primer sequence

<400> SEQUENCE: 8
gacggcaata aatcttccat gag                                             23

<210> SEQ ID NO 9
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 9
cctttgagct cagcagatga a                                               21

<210> SEQ ID NO 10
<211> LENGTH: 19
<212> TYPE: DNA
<213> ORGANISM: Artificial Sequence
<220> FEATURE:
<223> OTHER INFORMATION: Synthetic primer sequence

<400> SEQUENCE: 10
gggttcctgc cctttgatt                                                  19

<210> SEQ ID NO 11
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 11
ttgggccaca cagtctctaa                                                 20

<210> SEQ ID NO 12
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 12
tgagttgctg tggctgtaat g                                               21
```

METHODS FOR ASSESSING RISK OF DEVELOPING COLORECTAL CANCER

CROSS-REFERENCE TO RELATED APPLICATIONS

This application is a § 371 national stage of PCT International Application No. PCT/AU2017/050066, filed Jan. 27, 2017, claiming priority of Australian Patent Application No. AU 2016900254, filed Jan. 28, 2016, and Australian Patent Application No. AU 2016903246, filed Aug. 16, 2016, the contents of each of which are hereby incorporated by reference into the application.

FIELD OF THE INVENTION

The present disclosure relates to methods and systems for assessing the risk of a human subject for developing colorectal cancer. These methods may be combined with the subjects clinical risk to improve risk analysis. Such methods may be used to assist decision making about appropriate colorectal cancer screening regimens.

REFERENCE TO A SEQUENCE LISTING

This application incorporates-by-reference nucleotide and/or amino acid sequences which are present in the file named "190131_90630_Substitute_Sequence_Listing_CAS.txt", which is 2.68 kilobytes in size, and was created Jan. 31, 2019 in the IBM-PC machine format, having an operating system capacity with MS-Windows, which is contained in the text file being separately filed with this Second Preliminary Amendment on Jan. 31, 2019.

BACKGROUND OF THE INVENTION

Colorectal cancer screening programs advocate administering tests to individuals across apparently healthy populations to identify individuals who have either pre-malignant or early stages of colorectal cancer so that they may benefit from prevention or early treatment. Screening tests can include fecal occult blood testing and colonoscopy. In the average risk population, screening based on fecal occult blood testing reduces colorectal mortality by 15% to 25% (Hewitson et al., 2007). Endoscopic screening can reduce mortality by 30% to 40% (Brenner et al., 2014).

Screening large numbers of the population can be costly. Ideally, deciding who should receive screening as well as the procedure and intensity of that screening should be based on the individual's risk of colorectal cancer. However, because there are currently no precise or valid methods to determine individual risk of the disease, targeted screening is only based on the very broad risk factors of age, gender, and sometimes, family history. This makes screening programs inefficient because many of those screened will never get colorectal cancer, and many of those not screened are at substantial risk of the disease (Ait Ouakrim et al., 2012).

Genetic risk assessments may increase screening program efficiency. However, genetic susceptibility to inherited colorectal cancer is complex and involves multiple variants and genes.

To increase screening efficiency and to decrease colorectal cancer mortality there s a requirement for improved methods for assessing the risk of a human subject for developing colorectal cancer.

SUMMARY OF THE INVENTION

The present inventors have identified SNP's within the genome that are useful for assessing the risk of a subject developing colorectal cancer.

Accordingly, in one aspect the present disclosure relates to a method for assessing the risk of a human subject for developing colorectal cancer comprising:

performing a genetic risk assessment of the subject, wherein the genetic risk assessment involves detecting, in a biological sample derived from the subject, the presence of at least 28 single nucleotide polymorphisms selected from Table 1, or a single nucleotide polymorphism in linkage disequilibrium with one or more thereof.

Some single nucleotide polymorphisms are more informative than others for a particular risk assessment. Thus, in an embodiment, the genetic risk assessment at least comprises detecting the presence of single nucleotide polymorphisms rs3987, rs35509282 and rs744166, or a single nucleotide polymorphism in linkage disequilibrium with one or more thereof.

In an embodiment, the genetic risk assessment comprises detecting more than 28 single nucleotide polymorphisms selected from Table 1, or a single nucleotide polymorphism in linkage disequilibrium with one or more thereof. For example, at least 29, at least 30, at least 31, at least 32, at least 33, at least 34, at least 35, at least 36, at least 37, at least 38, at least 39, at least 40, at least 41, at least 42, at least 43, at least 44 single nucleotide polymorphisms may be detected. In another embodiment, at least 45 single nucleotide polymorphisms are detected.

In another embodiment, the genetic risk assessment comprises detecting the presence of single nucleotide polymorphism rs5934683, or a single nucleotide polymorphism in linkage disequilibrium thereof.

In another embodiment, the genetic risk assessment is combined with a clinical risk assessment to obtain the risk of a human subject for developing colorectal cancer. In an example, the clinical risk assessment involves obtaining information from the subject on one or more of the following: medical history of colorectal cancer, age, family history of colorectal cancer, results of previous colonoscopy or sigmoidoscopy screening and race/ethnicity. In another example, the clinical risk assessment involves obtaining information from the subject on age and/or first degree relative's history of colorectal cancer. In an embodiment, family history of colorectal cancer includes multigenerational family history.

One of skill in the art will appreciate that the combined clinical risk assessment and genetic risk assessment defines the subjects overall risk for developing colon cancer. Thus, the methods of the invention can be used to assess overall risk.

In an embodiment, the methods of the present disclosure determine the absolute risk of a human female subject for developing colon cancer.

In another embodiment, the methods of the present disclosure determine the relative risk of a human female subject for developing colon cancer.

The methods of the present disclosure may be applicable to subjects with symptoms of colorectal cancer. For example, subjects that have had a positive fecal occult blood test can be assessed using the methods of the present disclosure. Fecal occult blood testing is generally recommended to subjects around 50 years of age. The present inventors have found that certain individuals are at increased risk of colorectal cancer well before they reach 50 years of age, in particular if a first degree relative has been diagnosed with colorectal cancer. These findings suggest that some individuals should be assessed earlier to determine whether they are at risk of colorectal cancer. Thus, in one embodiment, subjects assessed using the methods of the present disclosure are at least 40 years of age. In another embodiment, the subject assessed is by at least 30 years of age if a first degree relative has been diagnosed with colorectal cancer.

The subject may be male or female. In another embodiment, the subject is male.

Subjects determined to be at risk of developing colorectal cancer using the present invention may then be enrolled in a screening program or subjected to more frequent screening.

In an embodiment, performance of the disclosed methods is characterized by an area under the curve (AUC) of at least about 0.63.

In an embodiment, a single nucleotide polymorphism in linkage disequilibrium has linkage disequilibrium above 0.9. In another embodiment, a single nucleotide polymorphism in linkage disequilibrium has linkage disequilibrium of 1.

In another aspect, the methods of the present disclosure are used to determine the need for routine diagnostic testing of a human subject for colorectal cancer. For example, when factoring in that each of the single nucleotide polymorphisms may be present up to twice in the somatic diploid genome of the subject, a subject having at least 41, at least 42, at least 44, at least 46, at least 50, at least 55, at least 60, at least 65, or at least 70, of the single nucleotide polymorphisms should be enrolled in a fecal occult screening, colonoscopic or sigmoidoscopic screening program. In another embodiment, if the assessment places the subject in the top 20% of subjects in a population at risk of developing colorectal cancer the subject is enrolled in a fecal occult screening, colonoscopic or sigmoidoscopic screening program. In another embodiment, if the assessment places the subject in the top 10% of subjects in a population at risk of developing colorectal cancer the subject is enrolled in a fecal occult screening, colonoscopic or sigmoidoscopic screening program.

In a further aspect, the present invention provides a method of screening for colorectal cancer in a human subject, the method comprising assessing the risk of the subject for developing colorectal cancer using the method of the invention, and routinely screening for colorectal cancer in the subject if they are assessed as having a risk for developing colorectal cancer.

In another aspect, the methods of the present disclosure are used as an anti-colorectal cancer therapy for use in preventing colorectal cancer in a human subject at risk thereof.

In a further aspect, the present disclosure relates to a kit comprising at least 28 sets of primers for amplifying 28 or more nucleic acids, wherein the 28 or more nucleic acids comprise a single nucleotide polymorphism selected from Table 1, or a single nucleotide polymorphism in linkage disequilibrium with one or more thereof.

In another aspect, the present disclosure relates to a genetic array comprising at least 28 sets of probes for hybridising to 28 or more nucleic acids, wherein the 28 or more nucleic acids comprise a single nucleotide polymorphism selected from Table 1, or a single nucleotide polymorphism in linkage disequilibrium with one or more thereof.

In another aspect, the present disclosure relates to a computer implemented method for assessing the risk of a human subject for developing colorectal cancer, the method operable in a computing system comprising a processor and a memory, the method comprising:

receiving genetic risk data for the subject, wherein the genetic risk data was obtained by detecting, in a biological sample derived from the subject, the presence of at least 28 single nucleotide polymorphisms from Table 1, or a single nucleotide polymorphism in linkage disequilibrium with one or more thereof;

processing the data to determine the risk of the human subject for developing colorectal cancer;

outputting the risk of the human subject for developing colorectal cancer.

In an embodiment, the computer implemented method further comprises receiving clinical risk data for the subject;

processing the data to combine the clinical risk data with the genetic risk data to obtain the risk of the subject for developing colorectal cancer;

outputting the risk of the subject for developing colorectal cancer.

In an embodiment, the risk data for the subject is received from a user interface coupled to the computing system. In another embodiment, the risk data for the subject is received from a remote device across a wireless communications network. In another embodiment, the user interface or remote device is a SNP array platform. In another embodiment, outputting comprises outputting information to a user interface coupled to the computing system. In another embodiment, outputting comprises transmitting information to a remote device across a wireless communications network.

Any example herein shall be taken to apply mutatis mutandis to any other example unless specifically stated otherwise.

The present disclosure is not to be limited in scope by the specific examples described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The disclosure is hereinafter described by way of the following non-limiting Examples and with reference to the accompanying drawings.

BRIEF DESCRIPTION OF THE ACCOMPANYING DRAWINGS

FIG. 1. The simulated distribution of risk alleles for 1,000,000 people with a history of colorectal cancer (red) and 1,000,000 people without a history of colorectal cancer (blue); and the cumulative risk of colorectal cancer to age 70 years for the number of risk alleles for an Australian (square) and USA (circle) population.

FIGS. 2A-2D. Australian risks of colorectal cancer (males and females combined) by age category, family history of colorectal cancer (first-degree relative) and by number of risk alleles. 2A: cumulative risks to age 70 with highest and lowest quintiles for number of risk alleles. 2B: cumulative risks to age 70 with highest and lowest deciles for number of risk alleles. 2C: 5-year risks with highest and lowest quintiles for number of risk alleles. 2D: 5-year risks with highest and lowest deciles for number of risk alleles.

FIGS. 3A-3D. USA risks of colorectal cancer (males and females combined) by age category, family history of colorectal cancer (first-degree relative) and by number of risk alleles. 3A: cumulative risks to age 70 with highest and lowest quintiles for number of risk alleles. 3B: cumulative risks to age 70 with highest and lowest deciles for number of risk alleles. 3C: 5-year risks with highest and lowest quintiles for number of risk alleles. 3D: 5-year risks with highest and lowest deciles for number of risk alleles.

FIGS. 4A-4D. Australian risks of colorectal cancer (males) by age category, family history of colorectal cancer (first-degree relative) and by number of risk alleles. 4A: cumulative risks to age 70 with highest and lowest quintiles for number of risk alleles. 4B: cumulative risks to age 70 with highest and lowest deciles for number of risk alleles. 4C: 5-year risks with highest and lowest quintiles for number of risk alleles. 4D: 5-year risks with highest and lowest deciles for number of risk alleles.

FIGS. 5A-5D. Australian risks of colorectal cancer (females) by age category, family history of colorectal cancer (first-degree relative) and by number of risk alleles. 5A: cumulative risks to age 70 with highest and lowest quintiles for number of risk alleles. 5B: cumulative risks to age 70 with highest and lowest deciles for number of risk alleles. 5C: 5-year risks with highest and lowest quintiles for number of risk alleles. 5D: 5-year risks with highest and lowest deciles for number of risk alleles.

FIGS. 6A-6D. USA risks of colorectal cancer (males) by age category, family history of colorectal cancer (first-degree relative) and by number of risk alleles. 6A: cumulative risks to age 70 with highest and lowest quintiles for number of risk alleles. 6B: cumulative risks to age 70 with highest and lowest deciles for number of risk alleles. 6C: 5-year risks with highest and lowest quintiles for number of risk alleles. 6D: 5-year risks with highest and lowest deciles for number of risk alleles.

FIGS. 7A-7D. USA risks of colorectal cancer (females) by age category, family history of colorectal cancer (first-degree relative) and by number of risk alleles. 7A: cumulative risks to age 70 with highest and lowest quintiles for number of risk alleles. 7B: cumulative risks to age 70 with highest and lowest deciles for number of risk alleles. 7C: 5-year risks with highest and lowest quintiles for number of risk alleles. 7D: 5-year risks with highest and lowest deciles for number of risk alleles.

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., colorectal cancer analysis, molecular genetics, bioinformatics and biochemistry).

Unless otherwise indicated, the molecular and statistical techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

It is to be understood that this disclosure is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, optionally include plural referents unless the content clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule.

As used herein, the term "about", unless stated to the contrary, refers to +/−10%, more preferably +/−5%, more preferably +/−1%, of the designated value.

The term "and/or", e.g., "X and/or Y" shall be understood to mean either "X and Y" or "X or Y" and shall be taken to provide explicit support for both meanings or for either meaning.

As used herein, the term "colorectal cancer" encompasses any type of cancer that can develop in the colon or rectum of a subject. The terms "colorectal cancer", "colon cancer", "rectal cancer" and "bowel cancer" can be used interchangeably in the context of the present disclosure.

For example, the colorectal cancer may be characterised as T stage 1-4. In another example, the colorectal cancer may be characterised as Dukes stage A-D As used herein, "colorectal cancer" also encompasses a phenotype that displays a predisposition towards developing colorectal cancer in an individual. A phenotype that displays a predisposition for colorectal cancer, can, for example, show a higher likelihood that the cancer will develop in an individual with the phenotype than in members of a relevant general population under a given set of environmental conditions (diet, physical activity regime, geographic location, etc.). For example, the colorectal cancer may be classified clinically as pre-malignant (e.g. hyperplasia, adenoma).

A "polymorphism" is a locus that is variable; that is, within a population, the nucleotide sequence at a polymorphism has more than one version or allele. One example of a polymorphism is a "single nucleotide polymorphism", which is a polymorphism at a single nucleotide position in a genome (the nucleotide at the specified position varies between individuals or populations).

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein, such reference may include derivatives of the DNA such as amplicons, RNA transcripts thereof, etc.

The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. An allele "positively" correlates with a trait when it is linked to it and when presence of the allele is an indicator that the trait or trait form will occur in an individual comprising the allele. An allele "negatively" correlates with a trait when it is linked to it and when presence of the allele is an indicator that a trait or trait form will not occur in an individual comprising the allele. The term "risk allele" is used in the context of the present disclosure to refer to an allele indicating a genetic propensity to susceptibility to colorectal cancer. A subject can be homozygous, heterozygous or null for a particular risk allele.

A marker polymorphism or allele is "correlated" or "associated" with a specified phenotype (colorectal cancer susceptibility, etc.) when it can be statistically linked (positively or negatively) to the phenotype. Methods for determining whether a polymorphism or allele is statistically linked are known to those in the art. That is, the specified polymorphism(s) occurs more commonly in a case population (e.g., colorectal cancer patients) than in a control population (e.g., individuals that do not have colorectal cancer). This correlation is often inferred as being causal in nature, but it need not be-simple genetic linkage to (association with) a locus for a trait that underlies the phenotype is sufficient for correlation/association to occur.

The phrase "linkage disequilibrium" (LD) is used to describe the statistical correlation between two neighbouring polymorphic genotypes. Typically, LD refers to the correlation between the alleles of a random gamete at the two loci, assuming Hardy-Weinberg equilibrium (statistical independence) between gametes. LD is quantified with either Lewontin's parameter of association (D') or with Pearson correlation coefficient (r) (Devlin and Risch, 1995). Two loci with a LD value of 1 are said to be in complete LD. At the other extreme, two loci with a LD value of 0 are termed to be in linkage equilibrium. Linkage disequilibrium is calculated following the application of the expectation maximization algorithm (EM) for the estimation of haplotype frequencies (Slatkin and Excoffier, 1996). LD values according to the present disclosure for neighbouring genotypes/loci are selected above 0.5, more preferably, above 0.6, still more preferably, above 0.7, preferably, above 0.8, more preferably above 0.9, ideally about 1.0. Many of the SNPs in linkage disequilibrium with the SNPs of the present disclosure that are described herein have LD values of 0.9 or 1.

Another way one of skill in the art can readily identify SNPs in linkage disequilibrium with the SNPs of the present disclosure is determining the LOD score for two loci. LOD stands for "logarithm of the odds", a statistical estimate of whether two genes, or a gene and a disease gene, are likely to be located near each other on a chromosome and are therefore likely to be inherited. A LOD score of between about 2-3 or higher is generally understood to mean that two genes are located close to each other on the chromosome. Thus, in an embodiment, LOD values according to the present disclosure for neighbouring genotypes/loci are selected at least above 2, at least above 3, at least above 4, at least above 5, at least above 6, at least above 7, at least above 8, at least above 9, at least above 10, at least above 20 at least above 30, at least above 40, at least above 50.

In another embodiment, SNPs in linkage disequilibrium with the SNPs of the present disclosure can have a specified genetic recombination distance of less than or equal to about 20 centimorgan (cM) or less. For example, 15 cM or less, 10 cM or less, 9 cM or less, 8 cM or less, 7 cM or less, 6 cM or less, 5 cM or less, 4 cM or less, 3 cM or less, 2 cM or less, 1 cM or less, 0.75 cM or less, 0.5 cM or less, 0.25 cM or less, or 0.1 cM or less. For example, two linked loci within a single chromosome segment can undergo recombination during meiosis with each other at a frequency of less than or equal to about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.75%, about 0.5%, about 0.25%, or about 0.1% or less.

In another embodiment, SNPs in linkage disequilibrium with the SNPs of the present disclosure are within at least 100 kb (which correlates in humans to about 0.1 cM, depending on local recombination rate), at least 50 kb, at least 20 kb or less of each other.

One exemplary approach for the identification of surrogate markers for a particular SNP involves a simple strategy that presumes that SNPs surrounding the target SNP are in linkage disequilibrium and can therefore provide information about disease susceptibility. Potentially surrogate markers can therefore be identified from publicly available databases, such as HAPMAP, by searching for SNPs fulfilling certain criteria which have been found in the scientific community to be suitable for the selection of surrogate marker candidates.

"Allele frequency" refers to the frequency (proportion or percentage) at which an allele is present at a locus within an individual, within a line or within a population of lines. For example, for an allele "A," diploid individuals of genotype "AA," "Aa," or "aa" have allele frequencies of 1.0, 0.5, or 0.0, respectively. One can estimate the allele frequency within a line or population (e.g., cases or controls) by averaging the allele frequencies of a sample of individuals from that line or population. Similarly, one can calculate the allele frequency within a population of lines by averaging the allele frequencies of lines that make up the population.

In an embodiment, the term "allele frequency" is used to define the minor allele frequency (MAF). MAF refers to the frequency at which the least common allele occurs in a given population.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal position or region. For example, a polymorphic locus is a position or region where a polymorphic nucleic acid, trait determinant, gene or marker is located. In a further example, a "gene locus" is a specific chromosome location (region) in the genome of a species where a specific gene can be found.

A "marker," "molecular marker" or "marker nucleic acid" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, nRNA, mRNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Nucleic acids are "complementary" when they specifically hybridize in solution, e.g., according to Watson-Crick base pairing rules. A "marker locus" is a locus that can be used to track the presence of a second linked locus, e.g., a linked or correlated locus that encodes or contributes to the population variation of a phenotypic trait. For example, a marker locus can be used to monitor segregation of alleles at a locus, such as a quantitative trait locus (QTL), that are genetically or physically linked to the marker locus. Thus, a "marker allele," alternatively an "allele of a marker locus" is one of a plurality of polymorphic nucleotide sequences found at a marker locus in a population that is polymorphic for the marker locus.

In one embodiment, the present disclosure provides marker loci correlating with a phenotype of interest, e.g., colorectal cancer. Each of the identified markers is expected to be in close physical and genetic proximity (resulting in physical and/or genetic linkage) to a genetic element, e.g., a QTL that contributes to the relevant phenotype. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An "amplicon" is an amplified nucleic acid, e.g., a nucleic acid that is produced by amplifying a template nucleic acid by any available amplification method (e.g., PCR, LCR, transcription, or the like).

A specified nucleic acid is "derived from" a given nucleic acid when it is constructed using the given nucleic acid's sequence, or when the specified nucleic acid is constructed using the given nucleic acid.

A "gene" is one or more sequence(s) of nucleotides in a genome that together encode one or more expressed molecules, e.g., an RNA, or polypeptide. The gene can include coding sequences that are transcribed into RNA which may then be translated into a polypeptide sequence, and can include associated structural or regulatory sequences that aid in replication or expression of the gene.

A "genotype" is the genetic constitution of an individual (or group of individuals) at one or more genetic loci. Genotype is defined by the allele(s) of one or more known loci of the individual, typically, the compilation of alleles inherited from its parents.

A "haplotype" is the genotype of an individual at a plurality of genetic loci on a single DNA strand. Typically, the genetic loci described by a haplotype are physically and genetically linked, i.e., on the same chromosome strand.

A "set" of markers, probes or primers refers to a collection or group of markers probes, primers, or the data derived therefrom, used for a common purpose (e.g., assessing an individuals risk of developing colorectal cancer). Frequently, data corresponding to the markers, probes or primers, or derived from their use, is stored in an electronic medium. While each of the members of a set possess utility with respect to the specified purpose, individual markers selected from the set as well as subsets including some, but not all of the markers, are also effective in achieving the specified purpose.

The polymorphisms and genes, and corresponding marker probes, amplicons or primers described above can be embodied in any system herein, either in the form of physical nucleic acids, or in the form of system instructions that include sequence information for the nucleic acids. For example, the system can include primers or amplicons corresponding to (or that amplify a portion of) a gene or polymorphism described herein. As in the methods above, the set of marker probes or primers optionally detects a plurality of polymorphisms in a plurality of said genes or genetic loci. Thus, for example, the set of marker probes or primers detects at least one polymorphism in each of these genes, or any other polymorphism, gene or locus defined herein. Any such probe or primer can include a nucleotide sequence of any such polymorphism or gene, or a complementary nucleic acid thereof, or a transcribed product thereof (e.g., a nRNA or mRNA form produced from a genomic sequence, e.g., by transcription or splicing).

As used herein, "Receiver operating characteristic curves" refer to a graphical plot of the sensitivity vs. (1−specificity) for a binary classifier system as its discrimination threshold is varied. The ROC can also be represented equivalently by plotting the fraction of true positives (TPR=true positive rate) vs. the fraction of false positives (FPR=false positive rate). Also known as a Relative Operating Characteristic curve, because it is a comparison of two operating characteristics (TPR & FPR) as the criterion changes. ROC analysis provides tools to select possibly optimal models and to discard suboptimal ones independently from (and prior to specifying) the cost context or the class distribution. Methods of using in the context of the disclosure will be clear to those skilled in the art.

As used herein, the term "combining the genetic risk assessment with the clinical risk assessment to obtain the risk" refers to any suitable mathematical analysis relying on the results of the two assessments. For example, the results of the clinical risk assessment and the genetic risk assessment may be added, more preferably multiplied.

As used herein, the terms "routinely screening for colorectal cancer" and "more frequent screening" are relative terms, and are based on a comparison to the level of screening recommended to a subject who has no identified risk of developing colorectal cancer. For example, routine screening can include fecal occult screening, colonoscopy or sigmoidoscopy every one to two years. Various other time intervals for routine screening are discussed below.

Genetic Risk Assessment

In an embodiment, the methods of the present disclosure relate to assessing the risk of a subject for developing colorectal cancer by performing a genetic risk assessment.

The genetic risk assessment is performed by analysing the genotype of the subject at two or more loci for single nucleotide polymorphisms. For example, at least 28 single nucleotide polymorphisms can be detected. In other examples, at least 29, at least 30, at least 31, at least 32, at least 33, at least 34, at least 35, at least 36, at least 37, at least 38, at least 39, at least 40, at least 41, at least 42, at least 43, at least 44 single nucleotide polymorphisms are detected. In another example, at least 45 single nucleotide polymorphisms are detected.

As the skilled addressee will appreciate, each SNP which increases the risk of developing colorectal cancer has an odds ratio of association with colorectal cancer of greater than 1.0. In an embodiment, none of the polymorphisms have an odds ratio of association with colorectal cancer greater than 3 or greater than 4.

Examples of SNPs that can be detected as part of the genetic risk assessment include, but are not limited to, SNPs selected from the group consisting of rs72647484, rs10911251, rs6687758, 6691170, rs11903757, rs812481, rs35360328, rs10936599, rs3987, rs35509282, rs647161, rs1321311, rs16892766, rs6983267, rs10505477, rs7014346, rs719725, rs10904849, rs10795668, rs704017, rs11190164, rs1035209, rs12241008, rs174537, rs4246215, rs174550, rs1535, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, rs1800469, rs2241714, rs2423279, rs4813802, rs961253, rs6066825, rs4925386, rs5934683 or a SNP in linkage disequilibrium with one or more thereof. In an example, detected SNPs are selected from Table 1 or a single nucleotide polymorphism in linkage disequilibrium with one or more thereof. In an example, at least 28 SNPs from Table 1 or a single nucleotide polymorphism in linkage disequilibrium with one or more thereof are detected when performing the genetic risk assessment. In other examples, at least 29, at least 30, at least 31, at least 32, at least 33, at least 34, at least 35, at least 36, at least 37, at least 38, at least 39, at least 40, at least 41, at least 42, at least 43, at least 44 single nucleotide polymorphisms from Table 1 or a single nucleotide polymorphism in linkage disequilibrium with one or more thereof are detected. In another example, at least 45 single nucleotide polymorphisms from Table 1 or a single nucleotide polymorphism in linkage disequilibrium with one or more thereof are detected.

TABLE 1

SNPs associated with colorectal cancer. The table indicates the SNP nomenclature, the gene(s) closest to or within the likely regulatory target of the SNP, the reported risk allele genotype, the reported risk allele frequency in controls, the reported association with colorectal cancer per risk allele (odds ratio), the familial relative risk (FRR) attributable to the SNP, and the proportion of the log FRR due to the SNP. *Gene/s closest to or likely regulatory target of SNP. SNPs in linkage disequilibrium are shown in square brackets [ ].

| Locus | Gene* | SNP | Risk allele | Per risk allele OR | Freq of risk allele | FRR | Proportion of log FRR |
|---|---|---|---|---|---|---|---|
| 1p36.2 | WNT4; CDC42 | rs72647484 | T | 1.21 | 0.91 | 1.003 | 0.37% |
| 1q25.3 | LAMC1 | rs10911251 | A | 1.05 | 0.54 | 1.0006 | 0.07% |
| 1q41 | DUSP10; CICP13 | rs6687758, [rs6691170] | G | 1.09 | 0.2 | 1.0012 | 0.15% |
| 2q32.3 | NABP1; MYO1B; SDPR | rs11903757 | C | 1.06 | 0.36 | 1.003 | 0.37% |
| 3p14.1 | LRIG1 | rs812481 | G | 1.09 | 0.58 | 1.0018 | 0.22% |
| 3p22.1 | RP11; CTNNB1 | rs35360328 | A | 1.14 | 0.16 | 1.0023 | 0.29% |
| 3q26.2 | MYNN; TERC | rs10936599 | C | 1.08 | 0.75 | 1.0011 | 0.14% |
| 4q26 | NDST3 | rs3987 | C | 1.36 | 0.44 | 1.0235 | 2.87% |
| 4q32.2 | FSTL5 | rs35509282 | A | 1.53 | 0.09 | 1.0149 | 1.83% |
| 5q31.1 | PITX1; H2AFY | rs647161 | A | 1.11 | 0.67 | 1.0024 | 0.30% |
| 6p21.31 | CDKN1A | rs1321311 | A | 1.1 | 0.23 | 1.0016 | 0.20% |
| 8q23.3 | EIF3H | rs16892766 | C | 1.25 | 0.07 | 1.0032 | 0.40% |
| 8q24.21 | CCAT2; MYC | rs6983267 [rs10505477, rs7014346] | G | 1.21 | 0.52 | 1.0091 | 1.12% |
| 9q24 | TPD52L3; UHRF2 | rs719725 | A | 1.19 | 0.37 | 1.0011 | 0.13% |
| 10p13 | CUBN | rs10904849 | G | 1.14 | 0.68 | 1.0037 | 0.46% |
| 10p14 | GATA3 | rs10795668 | G | 1.12 | 0.67 | 1.0028 | 0.35% |
| 10q22.3 | ZMIZ1; AS1 | rs704017 | G | 1.06 | 0.57 | 1.0008 | 0.10% |
| 10q24.2 | SLC25A28; ENTPD7; COX15; CUTC; ABCC2 | rs11190164 [rs1035209] | G | 1.09 | 0.29 | 1.0015 | 0.19% |
| 10q25 | VTI1A | rs12241008 | C | 1.13 | 0.09 | 1.0012 | 0.15% |
| 11q12.2 | FADS1; FEN1 | 11qhap^; [rs174537, rs4246215, | G | 1.4 | 0.57 | 1.0281 | 3.41% |

TABLE 1-continued

SNPs associated with colorectal cancer. The table indicates the SNP
nomenclature, the gene(s) closest to or within the likely regulatory target of the SNP,
the reported risk allele genotype, the reported risk allele frequency in controls, the
reported association with colorectal cancer per risk allele (odds ratio), the familial
relative risk (FRR) attributable to the SNP, and the proportion of the log FRR due to
the SNP. *Gene/s closest to or likely regulatory target of SNP. SNPs in linkage
disequilibrium are shown in square brackets [ ].

| Locus | Gene* | SNP | Risk allele | Per risk allele OR | Freq of risk allele | FRR | Proportion of log FRR |
|---|---|---|---|---|---|---|---|
| | | rs174550, rs1535]. | | | | | |
| 11q13.4 | POLD3 | rs3824999 | G | 1.08 | 0.5 | 1.0015 | 0.18% |
| 11q23.1 | COLCA2 | rs3802842 | C | 1.11 | 0.29 | 1.0022 | 0.28% |
| 12p13.32 | CCND2 | rs3217810 | T | 1.2 | 0.16 | 1.0045 | 0.55% |
| 12p13.32 | CCND2 | rs3217901 | G | 1.1 | 0.41 | 1.0022 | 0.27% |
| 12p13.32 | CCND2 | rs10774214 | T | 1.09 | 0.38 | 1.0018 | 0.22% |
| 12q13.13 | DIP2B; ATF1 | rs11169552 | C | 1.09 | 0.72 | 1.0015 | 0.18% |
| 12q13.13 | LARP4; DIP2B | rs7136702 | T | 1.06 | 0.35 | 1.0008 | 0.10% |
| 12q24.12 | SH2B3 | rs3184504 | C | 1.09 | 0.53 | 1.0019 | 0.23% |
| 12q24.21 | TBX3 | rs59336 | T | 1.09 | 0.48 | 1.0019 | 0.23% |
| 12q24.22 | NOS1 | rs73208120 | G | 1.16 | 0.11 | 1.0021 | 0.26% |
| 14q22.2 | BMP4 | rs1957636 | T | 1.08 | 0.4 | 1.0014 | 0.18% |
| 14q22.2 | BMP4 | rs4444235 | C | 1.11 | 0.46 | 1.0027 | 0.33% |
| 15q13.3 | SCG5; GREM1 | rs11632715 | A | 1.12 | 0.47 | 1.0032 | 0.39% |
| 15q13.3 | SCG5; GREM1 | rs16969681 | T | 1.18 | 0.09 | 1.0022 | 0.28% |
| 16q22.1 | CDH1 | rs9929218 | G | 1.1 | 0.71 | 1.0019 | 0.23% |
| 16q24.1 | FOXL1 | rs16941835 | C | 1.15 | 0.21 | 1.0032 | 0.40% |
| 17q21 | STAT3 | rs744166 | G | 1.27 | 0.55 | 1.0142 | 1.74% |
| 18q21.1 | SMAD7 | rs4939827 | T | 1.18 | 0.52 | 1.0069 | 0.84% |
| 19q13.11 | RHPN2 | rs10411210 | C | 1.15 | 0.9 | 1.0018 | 0.22% |
| 19q13.2 | TMEM91; TGFB1 | 19qhap^; [rs1800469, rs2241714] | G | 1.16 | 0.49 | 1.0055 | 0.68% |
| 20p12.3 | FERMT1; BMP2 | rs2423279 | C | 1.14 | 0.3 | 1.0036 | 0.44% |
| 20p12.3 | FERMT1; BMP2 | rs4813802 | G | 1.09 | 0.36 | 1.0017 | 0.21% |
| 20p12.3 | FERMT1; BMP2 | rs961253 | A | 1.12 | 0.36 | 1.003 | 0.36% |
| 20q13.1 | PREX1 | rs6066825 | A | 1.09 | 0.64 | 1.0017 | 0.21% |
| 20q13.33 | LAMA5 | rs4925386 | C | 1.08 | 0.68 | 1.0013 | 0.16% |

In an example, single nucleotide polymorphisms in linkage disequilibrium with one or more of the single nucleotide polymorphisms selected from Table 1 have LD values of at least 0.5, at least 0.6, at least 0.7, at least 0.8. In another example, single nucleotide polymorphisms in linkage disequilibrium have LD values of at least 0.9. In another example, single nucleotide polymorphisms in linkage disequilibrium have LD values of at least 1.

Some single nucleotide polymorphisms are more informative than others for a particular risk assessment. For example, the genetic risk assessment may comprise detecting rs3987, rs35509282 and rs744166, or a single nucleotide polymorphism in linkage disequilibrium with one or more thereof.

In another example, the genetic risk assessment can comprise detecting rs72647484, rs10911251, rs6687758, rs11903757, rs812481, rs35360328, rs10936599, rs3987, rs35509282, rs647161, rs1321311, rs16892766, rs6983267, rs719725, rs10904849, rs10795668, rs704017, rs11190164, rs12241008, 11qhap (any one or all of rs174537, rs4246215, rs174550, and rs1535), rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, 19qhap^ (any one or all of rs1800469 and rs2241714), rs2423279, rs4813802, rs961253, rs6066825, rs4925386 or a single nucleotide polymorphism in linkage disequilibrium with one or more thereof.

In another example, the genetic risk assessment comprises detecting the presence of single nucleotide polymorphism rs5934683, or a single nucleotide polymorphism in linkage disequilibrium thereof.

In an embodiment, the number of SNPs assessed is based on the net reclassification improvement in risk prediction calculated using net reclassification index (NRI) (Pencina et al., 2008). In an embodiment, the net reclassification improvement of the methods of the present disclosure is greater than 0.01.

In a further embodiment, the net reclassification improvement of the methods of the present disclosure is greater than 0.05. In yet another embodiment, the net reclassification improvement of the methods of the present disclosure is greater than 0.1.

SNPs in linkage disequilibrium with those specifically mentioned herein are easily identified by those of skill in the art. Examples of such SNPs include four perfectly correlated SNPs within 11q12.2 (rs174537, rs4246215, rs174550, and rs1535). These four SNPs are named in the present disclosure as the 11q12.2 haplotype. Another example includes rs1800469 and rs2241714 which are located within 19q13.2.

These SNPs are also perfectly correlated and are named in the present disclosure as the 19q13.2 haplotype. Other examples include rs6687758 and rs6691170, located within 1q41; rs10505477, rs6983267 and rs7014346, located within 8q24.21; rs11632715 and rs16969681 located within 15q31; rs1035209, rs11190164 located within 10q24.2; rs11169552, rs7136702 located within 12q13.13 (further possible examples provided in Table 2).

TABLE 2

List of SNPs (correlated SNPs) in LD* with the top six risk SNPs (DbSNP). SNPs with an $r^2$ greater than 0.08 (African American, American, Asian, and European populations) in the HAPMAP dataset (http://hapmap.ncbi.nlm.nih.gov) are shown.

| DbSNP | DbSNP Position | Correlated SNP | Correlated SNP Position | $r^2$ | D' |
|---|---|---|---|---|---|
| rs16892766 | chr8: 117630683 | rs16888589 | chr8: 117635602 | 1 | 1 |
|  |  | rs11986063 | chr8: 117640315 | 0.85 | 0.98 |
| rs35509282 | chr4: 163333405 | rs11736440 | chr4: 163336693 | 0.99 | 1 |
|  |  | rs12508784 | chr4: 163333299 | 0.86 | 1 |
|  |  | rs12511058 | chr4: 163326723 | 0.84 | 1 |
|  |  | rs17042479 | chr4: 163325411 | 0.85 | 1 |
|  |  | rs17600575 | chr4: 163329336 | 0.85 | 1 |
|  |  | rs2122494 | chr4: 163331379 | 0.98 | 1 |
|  |  | rs57336275 | chr4: 163341215 | 0.98 | 1 |
|  |  | rs74964851 | chr4: 163338255 | 0.98 | 1 |
|  |  | rs79783178 | chr4: 163325957 | 0.88 | 1 |
|  |  | rs9998942 | chr4: 163340404 | 0.98 | 1 |
|  |  | rs12642547 | chr4: 163337313 | 0.85 | 0.99 |
|  |  | rs12645341 | chr4: 163337355 | 0.85 | 0.99 |
|  |  | rs59363334 | chr4: 163340796 | 0.85 | 0.99 |
|  |  | rs11100440 | chr4: 163324864 | 0.81 | 0.97 |
| rs3987 | chr4: 118759055 | rs10018600 | chr4: 118776858 | 0.99 | 1 |
|  |  | rs10026807 | chr4: 118761523 | 0.97 | 1 |
|  |  | rs10026879 | chr4: 118761446 | 0.87 | 1 |
|  |  | rs12643469 | chr4: 118775565 | 1 | 1 |
|  |  | rs4317266 | chr4: 118778909 | 0.99 | 1 |
|  |  | rs4597906 | chr4: 118758795 | 0.98 | 1 |
|  |  | rs5861370 | chr4: 118764485 | 0.94 | 1 |
|  |  | rs7676593 | chr4: 118763497 | 0.98 | 1 |
|  |  | rs7684690 | chr4: 118774949 | 0.93 | 1 |
|  |  | rs1459530 | chr4: 118746231 | 0.83 | 0.99 |
|  |  | rs1459528 | chr4: 118750348 | 0.85 | 0.99 |
|  |  | rs1459529 | chr4: 118750315 | 0.85 | 0.99 |
|  |  | rs1459531 | chr4: 118742872 | 0.82 | 0.99 |
|  |  | rs4240312 | chr4: 118734518 | 0.81 | 0.99 |
|  |  | rs4270637 | chr4: 118744735 | 0.82 | 0.99 |
|  |  | rs4382104 | chr4: 118752001 | 0.85 | 0.99 |
|  |  | rs4834639 | chr4: 118755142 | 0.82 | 0.99 |
|  |  | rs6852960 | chr4: 118741585 | 0.82 | 0.99 |
|  |  | rs4377658 | chr4: 118782785 | 0.81 | 0.98 |
|  |  | rs7685408 | chr4: 118752469 | 0.87 | 0.97 |
|  |  | rs12503813 | chr4: 118784946 | 0.88 | 0.96 |
|  |  | rs13147985 | chr4: 118786434 | 0.88 | 0.96 |
|  |  | rs151286737 | chr4: 118790567 | 0.87 | 0.96 |
|  |  | rs4353970 | chr4: 118752091 | 0.86 | 0.95 |
|  |  | rs6824201 | chr4: 118736905 | 0.83 | 0.93 |
|  |  | rs11098407 | chr4: 118733381 | 0.82 | 0.92 |
|  |  | rs11562851 | chr4: 118735934 | 0.82 | 0.92 |
|  |  | rs11562871 | chr4: 118733490 | 0.82 | 0.92 |
|  |  | rs1380373 | chr4: 118736995 | 0.82 | 0.92 |
|  |  | rs17865121 | chr4: 118733657 | 0.82 | 0.92 |
|  |  | rs11427328 | chr4: 118737132 | 0.82 | 0.92 |
|  |  | rs6856317 | chr4: 118784120 | 0.82 | 0.92 |
|  |  | rs4594794 | chr4: 118788352 | 0.82 | 0.91 |
|  |  | rs6823808 | chr4: 118787965 | 0.82 | 0.91 |
|  |  | rs70941133 | chr4: 118784105 | 0.81 | 0.91 |
| rs6983267 | chr8: 128413305 | rs10505474 | chr8: 128417504 | 0.84 | 1 |
|  |  | rs10808556 | chr8: 128413147 | 0.84 | 1 |
|  |  | rs10956366 | chr8: 128423491 | 0.83 | 1 |
|  |  | rs10956370 | chr8: 128424728 | 0.83 | 1 |
|  |  | rs11778075 | chr8: 128421128 | 0.84 | 1 |
|  |  | rs11784983 | chr8: 128421348 | 0.84 | 1 |
|  |  | rs11998706 | chr8: 128422098 | 0.84 | 1 |
|  |  | rs12678562 | chr8: 128422488 | 0.84 | 1 |
|  |  | rs2060776 | chr8: 128420117 | 0.84 | 1 |
|  |  | rs3847137 | chr8: 128414498 | 0.84 | 1 |
|  |  | rs3933712 | chr8: 128420265 | 0.84 | 1 |
|  |  | rs4276648 | chr8: 128427372 | 0.84 | 1 |
|  |  | rs4871022 | chr8: 128427720 | 0.84 | 1 |
|  |  | rs4871788 | chr8: 128421785 | 0.84 | 1 |
|  |  | rs4871789 | chr8: 128428061 | 0.84 | 1 |
|  |  | rs7013328 | chr8: 128423911 | 0.83 | 1 |
|  |  | rs7018367 | chr8: 128424883 | 0.82 | 1 |

TABLE 2-continued

List of SNPs (correlated SNPs) in LD* with the top six risk SNPs (DbSNP). SNPs with an $r^2$ greater than 0.08 (African American, American, Asian, and European populations) in the HAPMAP dataset (http://hapmap.ncbi.nlm.nih.gov) are shown.

| DbSNP | DbSNP Position | Correlated SNP | Correlated SNP Position | $r^2$ | D' |
|---|---|---|---|---|---|
| | | rs7018368 | chr8: 128424933 | 0.83 | 1 |
| | | rs7018371 | chr8: 128424899 | 0.82 | 1 |
| | | rs7837328 | chr8: 128423127 | 0.83 | 1 |
| | | rs7837626 | chr8: 128423341 | 0.83 | 1 |
| | | rs7837644 | chr8: 128423398 | 0.83 | 1 |
| | | rs7837706 | chr8: 128423184 | 0.83 | 1 |
| | | rs871135 | chr8: 128426393 | 0.84 | 1 |
| | | rs12682374 | chr8: 128410948 | 0.97 | 0.99 |
| rs72647484 | chr1: 122587728 | rs2744697 | chr1: 22583655 | 0.86 | 1 |
| | | rs2744742 | chr1: 22566927 | 0.83 | 1 |
| | | rs2744748 | chr1: 22573163 | 0.83 | 1 |
| | | rs2744752 | chr1: 22575306 | 0.83 | 1 |
| | | rs2744753 | chr1: 22576327 | 0.86 | 1 |
| | | rs2744754 | chr1: 22576467 | 0.86 | 1 |
| | | rs2744758 | chr1: 22578619 | 0.86 | 1 |
| | | rs2807329 | chr1: 22565060 | 0.83 | 1 |
| | | rs2807332 | chr1: 22566847 | 0.96 | 1 |
| | | rs2807334 | chr1: 22568696 | 0.96 | 1 |
| | | rs2807335 | chr1: 22573764 | 0.96 | 1 |
| | | rs2807340 | chr1: 22580473 | 0.81 | 1 |
| | | rs28617726 | chr1: 22586280 | 1 | 1 |
| | | rs72647481 | chr1: 22584718 | 0.86 | 1 |
| | | rs72647481 | chr1: 22584718 | 1 | 1 |
| | | rs72647483 | chr1: 22587009 | 0.86 | 1 |
| | | rs72647483 | chr1: 22587009 | 1 | 1 |
| | | rs72647488 | chr1: 22590009 | 0.81 | 1 |
| | | rs72647488 | chr1: 22590009 | 0.89 | 1 |
| | | rs72647489 | chr1: 22590125 | 0.81 | 1 |
| | | rs72647489 | chr1: 22590125 | 0.89 | 1 |
| | | rs2744723 | chr1: 22535288 | 0.85 | 0.92 |
| rs744166 | chr17: 40514201 | rs1026916 | chr17: 40529835 | 0.89 | 1 |
| | | rs11079043 | chr17: 40545770 | 0.93 | 1 |
| | | rs11440924 | chr17: 40517657 | 0.99 | 1 |
| | | rs12601611 | chr17: 40497828 | 0.93 | 1 |
| | | rs12602466 | chr17: 40511946 | 0.9 | 1 |
| | | rs12937642 | chr17: 40525760 | 0.92 | 1 |
| | | rs12942547 | chr17: 40527544 | 0.85 | 1 |
| | | rs12942611 | chr17: 40535184 | 1 | 1 |
| | | rs12943176 | chr17: 40496447 | 0.93 | 1 |
| | | rs12949918 | chr17: 40526273 | 0.81 | 1 |
| | | rs12950549 | chr17: 40496594 | 1 | 1 |
| | | rs13342031 | chr17: 40536871 | 0.93 | 1 |
| | | rs17884075 | chr17: 40541608 | 1 | 1 |
| | | rs17884090 | chr17: 40518396 | 1 | 1 |
| | | rs17885629 | chr17: 40525098 | 0.81 | 1 |
| | | rs17885741 | chr17: 40498944 | 1 | 1 |
| | | rs17886724 | chr17: 40496163 | 1 | 1 |
| | | rs1905340 | chr17: 40520390 | 0.93 | 1 |
| | | rs1905341 | chr17: 40520597 | 0.9 | 1 |
| | | rs2306581 | chr17: 40500265 | 1 | 1 |
| | | rs35314169 | chr17: 40515826 | 0.93 | 1 |
| | | rs35840966 | chr17: 40521204 | 1 | 1 |
| | | rs35901220 | chr17: 40528168 | 0.94 | 1 |
| | | rs35950888 | chr17: 40499198 | 1 | 1 |
| | | rs3736161 | chr17: 40497835 | 1 | 1 |
| | | rs3736162 | chr17: 40497839 | 0.92 | 1 |
| | | rs3736164 | chr17: 40539825 | 0.93 | 1 |
| | | rs3785898 | chr17: 40515120 | 0.93 | 1 |
| | | rs3816769 | chr17: 40498273 | 0.99 | 1 |
| | | rs3869549 | chr17: 40492540 | 0.9 | 1 |
| | | rs4103200 | chr17: 40507065 | 0.93 | 1 |
| | | rs4796647 | chr17: 40543992 | 0.91 | 1 |
| | | rs4796791 | chr17: 40530763 | 1 | 1 |
| | | rs58288833 | chr17: 40496701 | 0.9 | 1 |
| | | rs61454571 | chr17: 40538298 | 0.89 | 1 |
| | | rs62075772 | chr17: 40504250 | 1 | 1 |
| | | rs6503695 | chr17: 40499533 | 0.93 | 1 |
| | | rs6503696 | chr17: 40499804 | 0.93 | 1 |
| | | rs6503697 | chr17: 40501579 | 0.93 | 1 |
| | | rs7211777 | chr17: 40534075 | 1 | 1 |
| | | rs7214610 | chr17: 40521787 | 0.92 | 1 |
| | | rs7216516 | chr17: 40517675 | 0.83 | 1 |
| | | rs7217655 | chr17: 40496024 | 1 | 1 |
| | | rs7219059 | chr17: 40521670 | 0.92 | 1 |

TABLE 2-continued

List of SNPs (correlated SNPs) in LD* with the top six risk SNPs (DbSNP). SNPs with an $r^2$ greater than 0.08 (African American, American, Asian, and European populations) in the HAPMAP dataset (http://hapmap.ncbi.nlm.nih.gov) are shown.

| DbSNP | DbSNP Position | Correlated SNP | Correlated SNP Position | $r^2$ | D' |
|---|---|---|---|---|---|
| | | rs7219739 | chr17: 40531761 | 1 | 1 |
| | | rs7224007 | chr17: 40528786 | 0.92 | 1 |
| | | rs7224416 | chr17: 40528702 | 0.92 | 1 |
| | | rs8068748 | chr17: 40532701 | 1 | 1 |
| | | rs8069645 | chr17: 40494902 | 0.92 | 1 |
| | | rs8070763 | chr17: 40536396 | 1 | 1 |
| | | rs8071537 | chr17: 40530895 | 1 | 1 |
| | | rs8072391 | chr17: 40495390 | 1 | 1 |
| | | rs8073517 | chr17: 40503324 | 1 | 1 |
| | | rs8073836 | chr17: 40525719 | 0.99 | 1 |
| | | rs8075676 | chr17: 40505202 | 0.93 | 1 |
| | | rs8076051 | chr17: 40505134 | 1 | 1 |
| | | rs8081037 | chr17: 40499158 | 0.91 | 1 |
| | | rs957970 | chr17: 40519890 | 1 | 1 |
| | | rs957971 | chr17: 40519925 | 1 | 1 |
| | | rs9891119 | chr17: 40507980 | 1 | 1 |
| | | rs9895473 | chr17: 40515722 | 0.93 | 1 |
| | | rs9897389 | chr17: 40523725 | 0.85 | 1 |
| | | rs9912773 | chr17: 40510534 | 0.92 | 1 |
| | | rs9913597 | chr17: 40510316 | 1 | 1 |
| | | rs35455295 | chr17: 40496438 | 0.95 | 1 |
| | | rs3869550 | chr17: 40492887 | 0.96 | 1 |
| | | rs4796793 | chr17: 40542210 | 0.92 | 0.99 |
| | | rs11328125 | chr17: 40537526 | 0.91 | 0.98 |
| | | rs10706259 | chr17: 40492373 | 0.83 | 0.97 |
| | | rs2354155 | chr17: 40546652 | 0.84 | 0.96 |
| | | rs35561964 | chr17: 40536575 | 0.82 | 0.96 |
| | | rs34972443 | chr17: 40502074 | 0.83 | 0.93 |
| | | rs2128786 | chr17: 40547327 | 0.81 | 0.91 |

Clinical Risk Assessment

The methods of the present disclosure can comprise performing a clinical risk assessment of the subject. The results of the clinical risk assessment can be combined with the genetic risk assessment to obtain the risk of the subject for developing colorectal cancer.

Any suitable clinical risk assessment procedure can be used in the present disclosure. Preferably, the clinical risk assessment does not involve genotyping the subject at one or more loci. Nonetheless, the clinical risk assessment procedure may include obtaining information on mutations in the MLH1, MSH2 and MSH6 genes and microsatellite instability status.

In another embodiment, the clinical risk assessment procedure includes obtaining information from the subject on one or more of the following: medical history of colorectal cancer and/or polyps, age, family history of colorectal cancer and/or polyps and/or other cancer including the age of the relative at the time of diagnosis, results of previous colonoscopy and/or sigmoidoscopy, results of previous faecal occult blood test, weight, body mass index, height, sex, alcohol consumption history, smoking history, exercise history, diet (e.g. consumption of folate, vegetables, red meat, fruits, fibre, and saturated fats), prevalence of inflammatory bowel disease, race/ethnicity, aspirin and NSAID use, implementation of estrogen replacement and use of oral contraceptives. For example, the clinical risk assessment procedure can include obtaining information from the subject on first degree relative's history of colorectal cancer. In another example, the clinical risk assessment procedure includes obtaining information from the subject on age and/or first degree relative's history of colorectal cancer.

In an embodiment, the clinical risk assessment includes details regarding the family history of colorectal cancer of at least some, preferably all, first degree relatives.

In an embodiment, family history of colorectal cancer involves an analysis of multigenerational family history. As used herein, "multigenerational family history" refers to the analysis of 2 or more generations. Multigenerational family history may include an analysis of, for instance, across the same generation (for example cousins), and/or between generations (for example uncles and aunts). For instance, in an embodiment, the clinical risk assessment includes details regarding the family history of colorectal cancer of at least some, preferably all, second degree relatives. In another embodiment, the clinical risk assessment includes details regarding the family history of colorectal cancer of at least some, preferably all, second and third degree relatives.

In an embodiment, the clinical risk assessment procedure provides an estimate of the risk of the subject developing colorectal cancer during the next 5-year period (i.e. 5-year risk). In an example, the 5-year risk determined by the clinical risk assessment is between about 1% to about 3%. In another example, the 5-year risk determined by the clinical risk assessment is between about 1.5% to about 2%.

In an embodiment, the clinical risk assessment procedure provides an estimate of the risk of the subject developing colorectal cancer during the next 10-year period (i.e. 10-year risk). In an example, the 10-year risk determined by the clinical risk assessment is between about 1% to about 3%. In another example, the 5-year risk determined by the clinical risk assessment is between about 1.5% to about 2%.

In another embodiment, the clinical risk assessment procedure provides an estimate of the risk of the subject developing colorectal cancer up to age 70 (i.e. lifetime risk). In an example, the lifetime risk determined by the clinical risk assessment is between about 15% to about 30%. In another example, the lifetime determined by the clinical risk assessment is between about 20% to about 25%.

In another embodiment, performing the clinical risk assessment uses a model which calculates the absolute risk of developing colon cancer. For example, the absolute risk of developing colon cancer can be calculated using cancer incidence rates while accounting for the competing risk of dying from other causes apart from colon cancer. In an embodiment, the clinical risk assessment provides a 5-year absolute risk of developing colon cancer. In another embodiment, the clinical risk assessment provides a 10-year absolute risk of developing colon cancer.

Examples of clinical risk assessment procedures include, but are not limited to, the Harvard Cancer Risk Index, the National Cancer Institute's Colorectal Cancer Risk Assessment Tool, the Cleveland Clinic Tool, the Mismatch Repair probability model (also known as MMRpro), Colorectal Risk Prediction Tool (CRiPT) and the like (see, for example, Usher-Smith et al., 2015). A wide body of research, focused on high-risk mutations and phenotypic risk factors have been compiled into these exemplary risk prediction algorithms.

The Harvard Cancer Risk Index predicts a 10 year risk of developing colon cancer using family history data (first degree relatives with colon cancer), and environmental factors such as body mass index, aspirin use, cigarette smoking, history of inflammatory bowel disease, height, physical activity, estrogen replacement, use of oral contraceptives, and consumption of folate, vegetables, alcohol, red meat, fruits, fibre, and saturated fats. In an example, the clinical risk assessment procedure uses the Harvard Cancer Risk Index to predict the 10 year risk of the subject developing colon cancer.

The Colorectal Cancer Risk Assessment Tool predicts 5-, 10-, 20-year, and lifetime risks of developing colorectal cancer for people over 50 years of age based on age, sex, use of sigmoidoscopy and/or colonoscopy, current leisure time activity, use of aspirin and NSAIDs, history of cigarette smoking, body mass index, history of hormone replacement, and consumption of vegetables. In an example, the clinical risk assessment procedure uses the Colorectal Cancer Risk Assessment Tool to predict the 5 year risk of the subject developing colorectal cancer. In another example, the clinical risk assessment procedure uses the Colorectal Cancer Risk Assessment Tool to predict the 10 year risk of the subject developing colorectal cancer. In another example, the clinical risk assessment procedure uses the Colorectal Cancer Risk Assessment Tool to predict the 20 year risk of the subject developing colorectal cancer. In another example, the clinical risk assessment procedure uses the Colorectal Cancer Risk Assessment Tool to predict the lifetime risk of the subject developing colorectal cancer.

The Cleveland Clinic Tool provides a colorectal cancer risk score based on age, sex, ethnicity, weigth, height, use of sigmoidoscopy and/or colonoscopy, faecal occult blood test, cigarette smoking, exercise, history of colorectal cancer and polyps, and consumption of vegetables and fruits.

The MMRpro model predicts five year and lifetime risks of developing colorectal and endometrial cancer based on mutations in the MLH1, MSH2 and MSH6 genes, as well as environmental factors such as family history of the disease, microsatellite instability status, age, and ethnicity. In an example, the clinical risk assessment procedure uses the MMRpro model to predict the 5 year risk of the subject developing colorectal cancer. In another example, the clinical risk assessment procedure uses the MMRpro model to predict the lifetime risk of the subject developing colorectal cancer.

The Colorectal Risk Prediction Tool (CRiPT) model uses multi-generational family history using a mixed major gene polygenic model to estimate colorectal cancer risk.

Calculating Composite SNP Relative Risk "Genetic Risk"

An individual's "genetic risk" can be defined as the product of genotype relative risk values for each SNP assessed. A log-additive risk model can then be used to define three genotypes AA, AB, and BB for a single SNP having relative risk values of 1, OR, and $OR^2$, under a rare disease model, where OR is the previously reported disease odds ratio for the high-risk allele, B, vs the low-risk allele, A. If the B allele has frequency (p), then these genotypes have population frequencies of $(1-p)^2$, $2p(1-p)$, and $p^2$, assuming Hardy-Weinberg equilibrium. The genotype relative risk values for each SNP can then be scaled so that based on these frequencies the average relative risk in the population is 1. Specifically, given the unscaled population average relative risk:

$$(\mu)=(1-p)^2+2p(1-p)OR+p^2OR^2$$

Adjusted risk values $1/\mu$, $OR/\mu$, and $OR^2/\mu$ are used for AA, AB, and BB genotypes. Missing genotypes are assigned a relative risk of 1. The following formula can be used to define the genetic risk:

$$SNP_1 \times SNP_2 \times SNP_3 \times SNP_4 \times SNP_5 \times SNP_6 \times SNP_7 \times SNP_8,$$
etc.

Similar calculations can be performed for non-SNP polymorphisms.

An alternate method for calculating the composite SNP risk is described in Mavaddat et al. (2015). In this example, the following formula is used;

$$PRS=\beta_1 x_1+\beta_2 x_2+\ldots \beta_\kappa x_\kappa+\beta_r x_n$$

where $\beta_\kappa$ is the per-allele log odds ratio (OR) for colon cancer associated with the minor allele for SNP κ, and $x_\kappa$, the number of alleles for the same SNP (0, 1 or 2), n is the total number of SNPs and PRS is the polygenic risk score (which can also be referred to as composite SNP risk).

It is envisaged that the "risk" of a human subject for developing colorectal cancer can be provided as a relative risk (or risk ratio) or an absolute risk as required.

In an embodiment, the genetic risk assessment obtains the "relative risk" of a human subject for developing colorectal cancer. Relative risk (or risk ratio), measured as the incidence of a disease in individuals with a particular characteristic (or exposure) divided by the incidence of the disease in individuals without the characteristic, indicates whether that particular exposure increases or decreases risk. Relative risk is helpful to identify characteristics that are associated with a disease, but by itself is not particularly helpful in guiding screening decisions because the frequency of the risk (incidence) is cancelled out.

In another embodiment, the genetic risk assessment obtains the "absolute risk" of a human subject for developing colorectal cancer. Absolute risk is the numerical probability of a human subject developing colorectal cancer within a specified period (e.g. 5, 10, 15, 20 or more years). It reflects a human subject's risk of developing colorectal cancer in so far as it does not consider various risk factors in isolation.

Combined Clinical Assessment×Genetic Risk

In combining the clinical risk assessment with the genetic risk assessment to obtain the "risk" of a human subject for developing colorectal cancer, the following formula can be used:

[Risk(*i.e.* Clinical Evaluation×*SNP* risk)]=[Clinical Evaluation risk]×$SNP_1$×$SNP_2$×$SNP_3$×$SNP_4$× $SNP_5$×$SNP_6$×$SNP_7$×$SNP_8$, . . . ×$SNP_{45}$ etc.

Where Clinical Evaluation is the risk provided by the clinical evaluation, and $SNP_1$ to $SNP_{45}$ are the relative risk for the individual SNPs, each scaled to have a population average of 1 as outlined above. Because the SNP risk values have been "centred" to have a population average risk of 1, if one assumes independence among the SNPs, then the population average risk across all genotypes for the combined value is consistent with the underlying Clinical Evaluation risk estimate.

In an embodiment the risk of a human subject for developing colorectal cancer is calculated by [Clinical Evaluation risk]×$SNP_1$×$SNP_2$×$SNP_3$×$SNP_4$×$SNP_5$×$SNP_6$×$SNP_7$,× $SNP_8$, . . . ×$SNP_{45}$ etc. In another embodiment the risk of a human subject for developing colorectal cancer is calculated by [Clinical Evaluation 5-year risk]×$SNP_1$×$SNP_2$×$SNP_3$× $SNP_4$×$SNP_5$×$SNP_6$×$SNP_7$,×$SNP_8$, . . . ×$SNP_{45}$ etc.

In another embodiment the risk of a human subject for developing colorectal cancer is calculated by [Clinical Evaluation lifetime risk]×$SNP_1$×$SNP_2$×$SNP_3$×$SNP_4$× $SNP_5$×$SNP_6$×$SNP_7$,×$SNP_8$, . . . ×$SNP_{45}$ etc. In an embodiment, the Clinical Evaluation is performed by assessing one or more of the following: medical history of colorectal cancer, age, family history of colorectal cancer, results of previous colonoscopy/sigmoidoscopy and race/ethnicity to provide a clinical risk. In this embodiment, the risk (i.e. combined genetic risk×clinical risk) is provided by:

[Risk(*i.e.* clinical×genetic risk)]=[clinical factor$_1$× clinical factor$_2$, . . . ,×clinical factor$_5$]×$SNP_1$× $SNP_2$×$SNP_3$×$SNP_4$×$SNP_5$×$SNP_6$×$SNP_7$,× $SNP_8$, . . . ×$SNP_{45}$etc.

In an embodiment, the Clinical Evaluation is performed by assessing first degree relatives history of colorectal cancer to provide a clinical risk. In this embodiment, the risk (i.e. combined genetic risk×clinical risk) is provided by:

[Risk(*i.e.* clinical×genetic risk)]=[clinical risk associated with a having a first degree relative with colorectal cancer]×$SNP_1$×$SNP_2$×$SNP_3$×$SNP_4$× $SNP_5$×$SNP_6$×$SNP_7$,×$SNP_8$, . . . ×$SNP_{45}$etc.

In an embodiment, the proportion of log familial relative risk (FRR; the odds ratio for colorectal cancer associated with having a first-degree relative with colorectal cancer) that could be attributable to the risk alleles of the SNPs can be estimated (assuming detection of 45 SNPs, Hardy-Weinberg equilibrium for each SNP, linkage equilibrium between the SNPs, and a multiplicative model for the associations of the SNPs with colorectal cancer risk). $SNP_1$, . . . $SNP_{45}$ are SNPs from Table 1 and clinical$_{46}$, . . . clinical$_m$ are clinical factors (note: these could be any heritable factors contributing to the FRR). Then if $G_i$ is a random variable giving the number of risk alleles at $SNP_i$ for a random person from the population, then $G_1, \ldots, G_m$ are all independent random variables (by linkage equilibrium) and the log-odds ratio for a random person is $X_1+ \ldots +X_m$ (by the assumed multiplicative model), where $X_i$=$G_i$log$OR_i$ and $OR_i$ is the per-allele odds ratio for $SNP_i$. A formula of Antoniou et al. 2003 derived rigorously in Win et al. 2014 then becomes log-FRR=½[Var($X_i$)+ . . . +Var($X_m$)]. This shows that the log FRR is the sum of independent components from the known and unknown colorectal cancer-associated SNPs. The proportion of the log FRR due to the known SNPs is ½[Var($X_1$)+ . . . +Var($X_{45}$)/logFRR, while the proportion due to clinical factor(s) is one minus this value. Additional clinical factors can be incorporated into the above calculation as required.

In an embodiment, the genetic risk assessment is combined with the clinical risk assessment to obtain the "relative risk" of a human subject for developing colorectal cancer. In another embodiment, the genetic risk assessment is combined with the clinical risk assessment to obtain the "absolute risk" of a human subject for developing colorectal cancer.

Subjects

The term "subject" as used herein refers to a human subject. Terms such as "subject", "patient" or "individual" are terms that can, in context, be used interchangeably in the present disclosure. In an example, the methods of the present disclosure can be used for routine screening of subjects. Routine screening can include testing subjects at pre-determined time intervals. Exemplary time intervals include screening monthly, quarterly, six monthly, yearly, every two years or every three years.

Current risk data suggests that the average person meets the risk-threshold for fecal occult blood test screening (which most national screening programs recommend) at around 50 years of age. However, the present inventors have found using the methods of the present disclosure that some individuals should be subject to fecal occult blood test screening well before they reach 50 years of age, in particular if a first degree relative of these subjects has been diagnosed with colorectal cancer. These findings suggest that subjects less than 50 years of age should be assessed using the methods of the present disclosure. Accordingly, in an example, subjects screened using the methods of the present disclosure are at least 38, at least 39, at least 40, at least 41, at least 42, at least 43, at least 44, at least 45, at least 46, at least 47, at least 48, at least 49 years of age. In an example, the subject is at least 40 years of age.

Subjects that have a family history of colorectal cancer can be screened earlier. For example, these subjects can be screened from at least 30, at least 31, at least 32, at least 33, at least 34, at least 35, at least 36, at least 37 years of age or older.

In another example, subjects assessed using the methods of the present disclosure have had a positive fecal occult blood test. In other examples, subjects have a personal history of adenomatous polyps or a personal history of inflammatory bowel disease (ulcerative colitis or Crohn's disease).

In another example, the methods of the present disclosure can be used to assess the risk of a human subject for developing colorectal cancer with symptoms that may be indicative of colorectal cancer. In the context of colorectal cancer, the present disclosure would be applicable to a subject with a positive fecal occult screening test or a subject presenting to the clinic with symptoms such change in bowel habits, including diarrhea or constipation, change in the stool consistency, rectal bleeding, persistent abdominal discomfort, such as cramps, incomplete bowel movement, gas or pain.

The methods of the present disclosure can be used to assess risk in male and female subjects. However, in an example, the subject is male.

The methods of the present disclosure can be used for assessing the risk for developing colorectal cancer in human subjects from various ethnic backgrounds. It is well known that over time there has been blending of different ethnic origins. While in practice, this does not influence the ability of a skilled person to practice the methods described herein, it may be desirable to identify the subject's ethnic background. In this instance, the ethnicity of the human subject can be self-reported by the subject. As an example, subjects can be asked to identify their ethnicity in response to this question: "To what ethnic group do you belong?" In another example, the ethnicity of the subject can be derived from medical records after obtaining the appropriate consent from the subject or from the opinion or observations of a clinician.

In an example, the subject can be classified as Caucasoid, Australoid, Mongoloid and Negroid based on physical anthropology. In an embodiment, the subject can be Caucasian, African American, Hispanic, Asian, Indian, or Latino. In an example, the subject is Caucasian. For example, the subject can be European.

A subject of predominantly European origin, either direct or indirect through ancestry, with white skin is considered Caucasian in the context of the present disclosure. A Caucasian may have, for example, at least 75% Caucasian ancestry (for example, but not limited to, the subject having at least three Caucasian grandparents).

A subject of predominantly central or southern African origin, either direct or indirect through ancestry, is considered Negroid in the context of the present disclosure. A Negroid may have, for example, at least 75% Negroid ancestry. An American subject with predominantly Negroid ancestry and black skin is considered African American in the context of the present disclosure. An African American may have, for example, at least 75% Negroid ancestry. Similar principle applies to, for example, subjects of Negroid ancestry living in other countries (for example Great Britain, Canada or the Netherlands).

A subject predominantly originating from Spain or a Spanish-speaking country, such as a country of Central or Southern America, either direct or indirect through ancestry, is considered Hispanic in the context of the present disclosure. A Hispanic subject may have, for example, at least 75% Hispanic ancestry.

Routine Screening

Fecal occult blood testing and colonoscopy/sigmoidoscopy reduces mortality from colorectal cancer but are expensive to routinely offer to large numbers of subjects. Accordingly, identifying the right population to screen is desirable. In an example, the methods of the present disclosure can be used for determining the need for routine diagnostic testing of a human subject for colorectal cancer. Such routine screening can include either fecal occult blood testing or colonoscopy/sigmoidoscopy at pre-determined time intervals such as those discussed above.

In an example, the need for routine diagnostic testing of a human subject for colorectal cancer is determined based on the number risk alleles detected. One of skill in the art would appreciate that each of the single nucleotide polymorphisms may be present up to twice in the somatic diploid genome of the subject. Thus, for example, an assessment of 28 single nucleotide polymorphisms may result in the detection of 56 alleles. In another example, an assessment of 45 single nucleotide polymorphisms may result in the detection of 90 alleles. A proportion of the detected alleles may be risk alleles. The number of risk alleles detected is relevant for the subject's risk of developing a colon cancer.

In an example, when factoring in that each of the single nucleotide polymorphisms may be present up to twice in the somatic diploid genome of the subject, subject having at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60 or more risk alleles of the single nucleotide polymorphisms should be enrolled in a fecal occult screening, colonoscopic or sigmoidoscopic screening program. For example, subjects with at least 44 risk alleles of the single nucleotide polymorphisms should be enrolled in a fecal occult screening, colonoscopic or sigmoidoscopic screening program. In an example, subjects at least 49 years of age with at least 44 risk alleles of the single nucleotide polymorphisms should be enrolled in a colonoscopic or sigmoidoscopic screening program.

In another example, subjects with at least 46 risk alleles of the single nucleotide polymorphisms should be enrolled in a fecal occult screening, colonoscopic or sigmoidoscopic screening program. In this example, subjects at least 47 years of age with at least 46 risk alleles of the single nucleotide polymorphisms should be enrolled in a colonoscopic or sigmoidoscopic screening program.

In another example, the need for routine diagnostic testing of a human subject for colorectal cancer is determined based on the subjects risk ranking within a population of subjects. For example, if the assessment places the subject in the top 30, 29, 28, 27, 26, 25, 24, 23, 22, 21, 20, 19, 18, 17, 16, 15, 14, 13, 12, 11, 10, 9, 8, 7, 6, 5, 4, 3, 2, 1% of subjects in a population at risk of developing colorectal cancer, then the subject is enrolled in a fecal occult screening, colonoscopic or sigmoidoscopic screening program.

In an example, the genetic risk is calculated based on: $SNP_1 \times SNP_2 \times SNP_3 \times SNP_4 \times SNP_5 \times SNP_6 \times SNP_7, \times SNP_x$ and subjects having a risk greater than about 5.9% are enrolled in a fecal occult screening, colonoscopic or sigmoidoscopic screening program. In another example, subjects having a risk greater than about 6.0, 6.1, 6.2, 6.3, 6.4, 6.5, 6.5, 6.6, 6.7, 6.8, 6.9, 7.0, 7.1, 7.2, 7.3, 7.4% or more are enrolled in a fecal occult screening, colonoscopic or sigmoidoscopic screening program.

In another example, the combined risk (i.e. clinical× genetic risk) is calculated based on: [clinical risk associated with a having a first degree relative with colorectal cancer]× $SNP_1 \times SNP_2 \times SNP_3 \times SNP_4 \times SNP_5 \times SNP_6 \times SNP_7, \times SNP_x$ and subjects having a risk greater than about 11.5% are enrolled in a fecal occult screening, colonoscopic or sigmoidoscopic screening program. In another example, subjects having a risk greater than about 12, 12.5, 13, 13.1, 13.2, 13.3, 13.4, 13.5, 14% or more are enrolled in a fecal occult screening, colonoscopic or sigmoidoscopic screening program.

In another example, the methods of the present disclosure are incorporated into a method of screening for colorectal cancer in a subject. In this example, the risk of a subject for developing colorectal cancer is assessed using the methods of the present disclosure and the subject is routinely screened for colorectal cancer via colonoscopy or sigmoidoscopy if they are assessed as having a risk for developing colorectal cancer.

The methods of the present disclosure can also be used in combination with other methods or "additional test(s)" in providing an evaluation of the risk of developing colorectal cancer. In this example, results of multiple tests may assist a clinician in determining whether a more definitive test such as a colonoscopy or sigmoidoscopy is required. In an example, the methods of the present disclosure are performed in combination with a fecal occult blood test.

Method Performance

In various embodiments the method performance is characterized by an area under the curve (AUC) of at least about 0.61, at least about 0.62, at least about 0.63.

In various embodiments, the sensitivity achieved by the methods of the present disclosure is at least about 50%, at least about 60%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%.

In various embodiments, the specificity achieved by the methods of the present disclosure is at least about 50%, at least about 60%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%.

Treatment

A high genetic propensity for colorectal cancer can be treated as a warning to commence prophylactic or therapeutic treatment. Thus, after performing the methods of the present disclosure treatment may be prescribed or administered to the subject. In an embodiment, the methods of the present disclosure relate to an anti-colorectal cancer therapy for use in preventing or reducing the risk of colorectal cancer in a human subject at risk thereof. In this embodiment, the subject may be prescribed or administered a therapeutic or prophylactic agent. For example, the subject may be prescribed or administered a chemopreventative. In other examples, the subject may be prescribed or administered nonsteroidal anti-inflammatory drug(s) such as aspirin, buprofen, acetaminophen, and naproxen or hormone therapy (estrogen plus progestin). In another example, treatment may include behavioural intervention such as manipulation of the subjects diet. Exemplary dietary modifications include increased fibre, mono-saturated fatty acids and/or fish oil.

Sample Preparation and Analysis

In performing the methods of the present disclosure, a biological sample from a subject is required. It is considered that terms such as "sample" and "specimen" are terms that can, in context, be used interchangeably in the present disclosure. Any biological material can be used as the above-mentioned sample so long as it can be derived from the subject and DNA can be isolated and analyzed according to the methods of the present disclosure. Samples are typically taken, following informed consent, from a patient by standard medical laboratory methods. The sample may be in a form taken directly from the patient, or may be at least partially processed (purified) to remove at least some non-nucleic acid material.

Exemplary "biological samples" include bodily fluids (blood, saliva, urine etc.), biopsy, tissue, and/or waste from the patient. Thus, tissue biopsies, stool, sputum, saliva, blood, lymph, tears, sweat, urine, vaginal secretions, or the like can easily be screened for SNPs, as can essentially any tissue of interest that contains the appropriate nucleic acids. In one embodiment, the biological sample is a cheek cell sample.

In another embodiment the sample is a blood sample. A blood sample can be treated to remove particular cells using various methods such as such centrifugation, affinity chromatography (e.g. immunoabsorbent means), immunoselection and filtration if required. Thus, in an example, the sample can comprise a specific cell type or mixture of cell types isolated directly from the subject or purified from a sample obtained from the subject. In an example, the biological sample is peripheral blood mononuclear cells (pBMC). Various methods of purifying sub-populations of cells are known in the art. For example, pBMC can be purified from whole blood using various known Ficoll based centrifugation methods (e.g. Ficoll-Hypaque density gradient centrifugation).

DNA can be extracted from the sample for detecting SNPs. In an example, the DNA is genomic DNA. Various methods of isolating DNA, in particular genomic DNA are known to those of skill in the art. In general, known methods involve disruption and lysis of the starting material followed by the removal of proteins and other contaminants and finally recovery of the DNA. For example, techniques involving alcohol precipitation; organic phenol/chloroform extraction and salting out have been used for many years to extract and isolate DNA. There are various commercially available kits for genomic DNA extraction (Qiagen, Life technologies; Sigma). Purity and concentration of DNA can be assessed by various methods, for example, spectrophotometry.

Marker Detection Strategies

Amplification primers for amplifying markers (e.g., marker loci) and suitable probes to detect such markers or to genotype a sample with respect to multiple marker alleles can be used in the disclosure. For example, primer selection for long-range PCR is described in U.S. Ser. No. 10/042,406 and U.S. Ser. No. 10/236,480; for short-range PCR, U.S. Ser. No. 10/341,832 provides guidance with respect to primer selection. Also, there are publicly available programs such as "Oligo" available for primer design. With such available primer selection and design software, the publicly available human genome sequence and the polymorphism locations, one of skill in the art can construct primers to amplify the SNPs to practice the disclosure. Further, it will be appreciated that the precise probe to be used for detection of a nucleic acid comprising a SNP (e.g., an amplicon comprising the SNP) can vary, e.g., any probe that can identify the region of a marker amplicon to be detected can be used in conjunction with the present disclosure. Further, the configuration of the detection probes can, of course, vary.

Examples of oligonucleotide primers useful for amplifying nucleic acids comprising SNPs known to be associated with a colorectal cancer are provided in Table 3. As the skilled person will appreciate, the sequence of the genomic region to which these oligonucleotides hybridize can be used to design primers which are longer at the 5' and/or 3' end, possibly shorter at the 5' and/or 3' (as long as the truncated version can still be used for amplification), which have one or a few nucleotide differences (but nonetheless can still be used for amplification), or which share no sequence similarity with those provided but which are designed based on genomic sequences close to where the specifically provided oligonucleotides hybridize and which can still be used for amplification.

TABLE 3

TaqMan primers and probes for the six highest risk SNPs shown in Table 1.

| SNP | Forward primer | Reverse primer |
|---|---|---|
| rs72647484 | TGCAGCAAGTGGTGAGAAG (SEQ ID NO: 1) | CCCATTGTTACCAGTATG AAGAGT (SEQ ID NO: 2) |
| rs3987 | AGACACTCTCCTCTGTTGA TTT (SEQ ID NO: 3) | GGACATCAAATAATGTGC CTAGAA (SEQ ID NO: 4) |

TABLE 3-continued

TaqMan primers and probes for the six
highest risk SNPs shown in Table 1.

| SNP | Forward primer | Reverse primer |
|---|---|---|
| rs35509282 | CCTGAGTAGCTGGGACTACA (SEQ ID NO: 5) | TCGAGACCATCCTGGCTAA (SEQ ID NO: 6) |
| rs16892766 | AACGGTCAGACGCAAACA (SEQ ID NO: 7) | GACGGCAATAAATCTTCCATGAG (SEQ ID NO: 8) |
| rs6983267 | CCTTTGAGCTCAGCAGATGAA (SEQ ID NO: 9) | GGGTTCCTGCCCTTTGATT (SEQ ID NO: 10) |
| rs744166 | TTGGGCCACACAGTCTCTAA (SEQ ID NO: 11) | TGAGTTGCTGTGGCTGTAATG (SEQ ID NO: 12) |

In some embodiments, the primers of the disclosure are radiolabelled, or labelled by any suitable means (e.g., using a non-radioactive fluorescent tag), to allow for rapid visualization of differently sized amplicons following an amplification reaction without any additional labelling step or visualization step. In some embodiments, the primers are not labelled, and the amplicons are visualized following their size resolution, e.g., following agarose or acrylamide gel electrophoresis. In some embodiments, ethidium bromide staining of the PCR amplicons following size resolution allows visualization of the different size amplicons.

It is not intended that the primers of the disclosure be limited to generating an amplicon of any particular size. For example, the primers used to amplify the marker loci and alleles herein are not limited to amplifying the entire region of the relevant locus, or any subregion thereof. The primers can generate an amplicon of any suitable length for detection. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Amplicons of any size can be detected using the various technologies described herein. Differences in base composition or size can be detected by conventional methods such as electrophoresis.

Indeed, it will be appreciated that amplification is not a requirement for marker detection, for example one can directly detect unamplified genomic DNA simply by performing a Southern blot on a sample of genomic DNA.

Typically, molecular markers are detected by any established method available in the art, including, without limitation, allele specific hybridization (ASH), detection of single nucleotide extension, array hybridization (optionally including ASH), or other methods for detecting single nucleotide polymorphisms, amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, and single-strand conformation polymorphisms (SSCP) detection.

Some techniques for detecting genetic markers utilize hybridization of a probe nucleic acid to nucleic acids corresponding to the genetic marker (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) and Sambrook et al. (supra).

PCR detection using dual-labelled fluorogenic oligonucleotide probes, commonly referred to as "TaqMan™" probes, can also be performed according to the present disclosure. These probes are composed of short (e.g., 20-25 bases) oligodeoxynucleotides that are labelled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO 92/02638.

Other similar methods include e.g. fluorescence resonance energy transfer between two adjacently hybridized probes, e.g., using the "LightCycler®" format described in U.S. Pat. No. 6,174,670.

Array-based detection can be performed using commercially available arrays, e.g., from Affymetrix (Santa Clara, Calif.) or other manufacturers. Reviews regarding the operation of nucleic acid arrays include Sapolsky et al. (1999); Lockhart (1998); Fodor (1997a); Fodor (1997b) and Chee et al. (1996). Array based detection is one preferred method for identification markers of the disclosure in samples, due to the inherently high-throughput nature of array based detection.

The nucleic acid sample to be analyzed is isolated, amplified and, typically, labelled with biotin and/or a fluorescent reporter group. The labelled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labelled nucleic acid, which is now bound to the probe array. Probes that most clearly match the labelled nucleic acid produce stronger signals than those that have mismatches. Since the sequence and position of each probe on the array are known, by complementarity, the identity of the nucleic acid sample applied to the probe array can be identified.

Correlating Markers to Cancer Risk

Correlations between SNPs and risk of colorectal cancer can be performed by any method that can identify a relationship between an allele and increased cancer risk, or a combination of alleles and increased cancer risk. For example, alleles in genes or loci defined herein can be correlated with increased risk of colorectal cancer. Most typically, these methods involve referencing a look up table that comprises correlations between alleles of the polymorphism and the cancer risk. The table can include data for multiple allele-risk relationships and can take account of additive or other higher order effects of multiple allele-risk relationships, e.g., through the use of statistical tools such as principle component analysis, heuristic algorithms, etc.

Correlation of a marker to a cancer risk optionally includes performing one or more statistical tests for correlation. Many statistical tests are known, and most are computer-implemented for ease of analysis. A variety of statistical methods of determining associations/correlations between phenotypic traits and biological markers are known and can be applied to the present disclosure. Hartl (1981). A variety of appropriate statistical models are described in Lynch and Walsh (1998). These models can, for example, provide for correlations between genotypic and phenotypic values, characterize the influence of a locus on cancer risk, sort out the relationship between environment and genotype, determine dominance or penetrance of genes, determine maternal and other epigenetic effects, determine principle components in an analysis (via principle component analysis, or "PCA"), and the like. The references cited in these texts provide considerable further detail on statistical models for correlating markers and cancer risk.

In addition to standard statistical methods for determining correlation, other methods that determine correlations by pattern recognition and training, such as the use of genetic algorithms, can be used to determine correlations between markers and cancer risk. This is particularly useful when identifying higher order correlations between multiple alleles and cancer risk. To illustrate, neural network approaches can be coupled to genetic algorithm-type programming for heuristic development of a structure-function data space model that determines correlations between genetic information and phenotypic outcomes.

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St. Peters, Mo.; partek.com), e.g., that provide software for pattern recognition (e.g., which provide Partek Pro 2000 Pattern Recognition Software).

Additional details regarding association studies can be found in U.S. Ser. No. 10/106,097, U.S. Ser. No. 10/042,819, U.S. Ser. No. 10/286,417, U.S. Ser. No. 10/768,788, U.S. Ser. No. 10/447,685, U.S. Ser. No. 10/970,761, and U.S. Pat. No. 7,127,355.

Systems for performing the above correlations are also a feature of the disclosure. Typically, the system will include system instructions that correlate the presence or absence of an allele (whether detected directly or, e.g., through expression levels) with a predicted cancer risk.

Optionally, the system instructions can also include software that accepts diagnostic information associated with any detected allele information, e.g., a diagnosis that a subject with the relevant allele has a particular cancer risk. This software can be heuristic in nature, using such inputted associations to improve the accuracy of the look up tables and/or interpretation of the look up tables by the system. A variety of such approaches, including neural networks, Markov modelling and other statistical analysis are described above.

Polymorphic Profiling

The disclosure provides methods of determining the polymorphic profile of an individual at the SNPs outlined in the present disclosure (Table 6) or SNPs in linkage disequilibrium with one or more thereof.

The polymorphic profile constitutes the polymorphic forms occupying the various polymorphic sites in an individual. In a diploid genome, two polymorphic forms, the same or different from each other, usually occupy each polymorphic site. Thus, the polymorphic profile at sites X and Y can be represented in the form X (x1, x1), and Y (y1, y2), wherein x1, x1 represents two copies of allele x1 occupying site X and y1, y2 represent heterozygous alleles occupying site Y.

The polymorphic profile of an individual can be scored by comparison with the polymorphic forms associated with susceptibility to colorectal cancer occurring at each site. The comparison can be performed on at least, e.g., 1, 2, 5, 10, 25, 50, or all of the polymorphic sites, and optionally, others in linkage disequilibrium with them. The polymorphic sites can be analyzed in combination with other polymorphic sites.

Polymorphic profiling is useful, for example, in selecting agents to affect treatment or prophylaxis of colorectal cancer in a given individual. Individuals having similar polymorphic profiles are likely to respond to agents in a similar way.

Computer Implemented Method

The methods of the present disclosure may be implemented by a system as a computer implemented method. For example, the system may be a computer system comprising one or a plurality of processors which may operate together (referred to for convenience as "processor") connected to a memory. The memory may be a non-transitory computer readable medium, such as a hard drive, a solid state disk or CD-ROM. Software, that is executable instructions or program code, such as program code grouped into code modules, may be stored on the memory, and may, when executed by the processor, cause the computer system to perform functions such as determining that a task is to be performed to assist a user to determine the risk of a human subject for developing colorectal cancer receiving data indicating the genetic risk and optionally the clinical risk of the subject developing colorectal cancer, wherein the genetic risk was derived by detecting, in a biological sample derived from the subject, the presence of at least 28 single nucleotide polymorphisms shown in Table 1 or a single nucleotide polymorphism in linkage disequilibrium with one or more thereof; processing the data to obtain the risk of a human subject for developing colorectal cancer; outputting the presence of the risk of a human subject for developing colorectal cancer.

For example, the memory may comprise program code which when executed by the processor causes the system to determine the presence of at least 28 single nucleotide polymorphisms selected from Table 1, or a single nucleotide polymorphism in linkage disequilibrium with one or more thereof, or receive data indicating the presence of at least 28 single nucleotide polymorphisms selected from Table 1, or a single nucleotide polymorphism in linkage disequilibrium with one or more thereof, process the data to obtain the risk of a human subject for developing colorectal cancer; report the risk of a human subject for developing colorectal cancer. Thus, in an embodiment, the program code causes the system to determine the "genetic risk".

In another example, the memory may comprise program code which when executed by the processor causes the system to determine the presence of at least 28 single nucleotide polymorphisms selected from Table 1, or a single nucleotide polymorphism in linkage disequilibrium with one or more thereof, or receive data indicating the presence of at least 28 single nucleotide polymorphisms selected from Table 1, or a single nucleotide polymorphism in linkage disequilibrium with one or more thereof and, receive or determine clinical risk data for the subject; process the data to combine the genetic risk data with the clinical risk data to obtain the risk of the subject for developing colorectal cancer; report the risk of a human subject for developing colorectal cancer. For example, the program code can cause the system to combine clinical risk assessment data×genetic risk.

In another embodiment, the system may be coupled to a user interface to enable the system to receive information from a user and/or to output or display information. For example, the user interface may comprise a graphical user interface, a voice user interface or a touchscreen. In an example, the user interface is a SNP array platform.

In an embodiment, the system may be configured to communicate with at least one remote device or server across a communications network such as a wireless communications network. For example, the system may be configured to receive information from the device or server across the communications network and to transmit information to the same or a different device or server across the communications network. In other embodiments, the system may be isolated from direct user interaction.

In another embodiment, performing the methods of the present disclosure to assess the risk of a subject for developing colorectal cancer, enables establishment of a diagnostic or prognostic rule based on the the genetic risk of the subject developing colorectal cancer. For example, the diagnostic or prognostic rule can be based on the genetic risk relative to a control, standard or threshold level of risk. In another example, the diagnostic or prognostic rule can be based on the combined genetic and clinical risk relative to a control, standard or threshold level of risk.

In another embodiment, the diagnostic or prognostic rule is based on the application of a statistical and machine learning algorithm. Such an algorithm uses relationships between a population of SNPs and disease status observed in training data (with known disease status) to infer relationships which are then used to determine the risk of a human subject for developing colorectal cancer in subjects with an unknown risk. An algorithm is employed which provides a risk of a human subject developing colorectal cancer. The algorithm performs a multivariate or univariate analysis function.

Kits and Products

In an embodiment, the present disclosure provides a kit comprising at least 28 sets of primers for amplifying 28 or more nucleic acids, wherein the 28 or more nucleic acids comprise a single nucleotide polymorphism selected from Table 1, or a single nucleotide polymorphism in linkage disequilibrium with one or more thereof.

In an embodiment, the kit comprises at least 28, at least 29, at least 30, at least 31, at least 32, at least 33, at least 34, at least 35, at least 36, at least 37, at least 38, at least 39, at least 40, at least 41, at least 42, at least 43, at least 44, at least 45 sets of the primers for amplifying nucleic acids comprising a single nucleotide polymorphism selected from Table 1, or a single nucleotide polymorphism in linkage disequilibrium with one or more thereof.

As would be appreciated by those of skill in the art, once a SNP is identified, primers can be designed to amplify the SNP as a matter of routine. Various software programs are freely available that can suggest suitable primers for amplifying SNPs of interest.

Again, it would be known to those of skill in the art that PCR primers of a PCR primer pair can be designed to specifically amplify a region of interest from human DNA. In the context of the present disclosure, the region of interest contains the single-base variation (e.g. single-nucleotide polymorphism, SNP) which shall be genotyped. Each PCR primer of a PCR primer pair can be placed adjacent to a particular single-base variation on opposing sites of the DNA sequence variation. Furthermore, PCR primers can be designed to avoid any known DNA sequence variation and repetitive DNA sequences in their PCR primer binding sites.

The kit may further comprise other reagents required to perform an amplification reaction such as a buffer, nucleotides and/or a polymerase, as well as reagents for extracting nucleic acids from a sample.

Array based detection is one preferred method for assessing the SNPs of the disclosure in samples, due to the inherently high-throughput nature of array based detection. A variety of probe arrays have been described in the literature and can be used in the context of the present disclosure for detection of SNPs that can be correlated to colorectal cancer. For example, DNA probe array chips are used in one embodiment of the disclosure. The recognition of sample DNA by the set of DNA probes takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present.

Thus, in another embodiment, the present disclosure provides a genetic array comprising at least 28 sets of probes for hybridising to 28 or more nucleic acids, wherein the 28 or more nucleic acids comprise a single nucleotide polymorphism selected from Table 1, or a single nucleotide polymorphism in linkage disequilibrium with one or more thereof. In an embodiment, the array comprises at least 28, at least 29, at least 30, at least 31, at least 32, at least 33, at least 34, at least 35, at least 36, at least 37, at least 38, at least 39, at least 40, at least 41, at least 42, at least 43, at least 44, at least 45 probes for hybridising to nucleic acids comprising a single nucleotide polymorphism selected from Table 1, or a single nucleotide polymorphism in linkage disequilibrium with one or more thereof.

Primers and probes for other SNPs can be included with the above exemplified kits. For example, primers and/or probes may be included for X chromosome SNP (rs5934683) or various other SNPs.

EXAMPLES

Example 1—SNPs Indicative of Colorectal Cancer Risk

54 SNPs associated with colorectal cancer in European populations were identified. Of these, four SNPs within 11q12.2 (rs174537, rs4246215, rs174550, and rs1535) are perfectly correlated and can be represented by a common haplotype (named here as the 11q12.2 haplotype). Two SNPs within 19q13.2 (rs1800469 and rs2241714) are perfectly correlated and can be represented by a common haplotype (named here as the 19q13.2 haplotype). One SNP is on the X chromosome (rs5934683) and was not included in the simulation of colorectal cancer risk for males and females combined. Two SNPs within 1q41 (rs6687758 and rs6691170) are in linkage disequilibrium. Thus, rs6691170 was excluded. Three SNPs within 8q24.21 (rs10505477, rs6983267, and rs7014346) have a D prime of 1.0. Thus, rs10505477 and rs7014346 were excluded. Two SNPs within 10q24.2 (rs1035209 and rs11190164) have a D prime of 0.9. Thus, rs1035209 was excluded.

Accordingly, 45 SNPs have been identified in total with remaining SNPs being in linkage disequilibrium thereof or on the X chromosome. SNPs indicative of colorectal cancer risk are shown in Table 4. The allele frequency of each risk allele and the odds ratio per risk allele is also shown in Table 4.

The average risk allele frequency was 0.43 (range 0.07 to 0.91). The average odds ratio per risk allele was 1.14 (range 1.05 to 1.53). The average familial relative risk (FRR; the odds ratio for colorectal cancer associated with having a first-degree relative with colorectal cancer) that could be attributed to each SNP was 1.0040 (range 1.0006 to 1.0281), which is 0.50% (range 0.07% to 3.41%) of the total log FRR. The combined FRR that could be attributable to all 45 SNPs was 1.1980, which is 22.3% of the total log FRR. The estimated FRR not due to the SNPs was 1.88.

TABLE 4

SNPs associated with colorectal cancer. The table indicates the SNP nomenclature, the gene(s) closest to or within the likely regulatory target of the SNP, the reported risk allele genotype, the reported risk allele frequency in controls, the reported association with colorectal cancer per risk allele (odds ratio), the familial relative risk (FRR) attributable to the SNP, and the proportion of the log FRR due to the SNP. *Gene/s closest to or likely regulatory target of SNP. SNPs in linkage disequilibrium are shown in square brackets [ ].

| Locus | Gene* | SNP | Risk allele | Per risk allele OR | Freq of risk allele | FRR | Proportion of log FRR |
|---|---|---|---|---|---|---|---|
| 1p36.2 | WNT4; CDC42 | rs72647484 | T | 1.21 | 0.91 | 1.003 | 0.37% |
| 1q25.3 | LAMC1 | rs10911251 | A | 1.05 | 0.54 | 1.0006 | 0.07% |
| 1q41 | DUSP10; CICP13 | rs6687758, [rs6691170] | G | 1.09 | 0.2 | 1.0012 | 0.15% |
| 2q32.3 | NABP1; MYO1B; SDPR | rs11903757 | C | 1.06 | 0.36 | 1.003 | 0.37% |
| 3p14.1 | LRIG1 | rs812481 | G | 1.09 | 0.58 | 1.0018 | 0.22% |
| 3p22.1 | RP11; CTNNB1 | rs35360328 | A | 1.14 | 0.16 | 1.0023 | 0.29% |
| 3q26.2 | MYNN; TERC | rs10936599 | C | 1.08 | 0.75 | 1.0011 | 0.14% |
| 4q26 | NDST3 | rs3987 | C | 1.36 | 0.44 | 1.0235 | 2.87% |
| 4q32.2 | FSTL5 | rs35509282 | A | 1.53 | 0.09 | 1.0149 | 1.83% |
| 5q31.1 | PITX1; H2AFY | rs647161 | A | 1.11 | 0.67 | 1.0024 | 0.30% |
| 6p21.31 | CDKN1A | rs1321311 | A | 1.1 | 0.23 | 1.0016 | 0.20% |
| 8q23.3 | EIF3H | rs16892766 | C | 1.25 | 0.07 | 1.0032 | 0.40% |
| 8q24.21 | CCAT2; MYC | rs6983267 [rs10505477, rs7014346] | G | 1.21 | 0.52 | 1.0091 | 1.12% |
| 9q24 | TPD52L3; UHRF2 | rs719725 | A | 1.19 | 0.37 | 1.0011 | 0.13% |
| 10p13 | CUBN | rs10904849 | G | 1.14 | 0.68 | 1.0037 | 0.46% |
| 10p14 | GATA3 | rs10795668 | G | 1.12 | 0.67 | 1.0028 | 0.35% |
| 10q22.3 | ZMIZ1; AS1 | rs704017 | G | 1.06 | 0.57 | 1.0008 | 0.10% |
| 10q24.2 | SLC25A28; ENTPD7; COX15; CUTC; ABCC2 | rs11190164 [rs1035209] | G | 1.09 | 0.29 | 1.0015 | 0.19% |
| 10q25 | VTI1A | rs12241008 | C | 1.13 | 0.09 | 1.0012 | 0.15% |
| 11q12.2 | FADS1; FEN1 | 11qhap^; [rs174537, rs4246215, rs174550, rs1535]. | G | 1.4 | 0.57 | 1.0281 | 3.41% |
| 11q13.4 | POLD3 | rs3824999 | G | 1.08 | 0.5 | 1.0015 | 0.18% |
| 11q23.1 | COLCA2 | rs3802842 | C | 1.11 | 0.29 | 1.0022 | 0.28% |
| 12p13.32 | CCND2 | rs3217810 | T | 1.2 | 0.16 | 1.0045 | 0.55% |
| 12p13.32 | CCND2 | rs3217901 | G | 1.1 | 0.41 | 1.0022 | 0.27% |
| 12p13.32 | CCND2 | rs10774214 | T | 1.09 | 0.38 | 1.0018 | 0.22% |
| 12q13.13 | DIP2B; ATF1 | rs11169552 | C | 1.09 | 0.72 | 1.0015 | 0.18% |
| 12q13.13 | LARP4; DIP2B | rs7136702 | T | 1.06 | 0.35 | 1.0008 | 0.10% |
| 12q24.12 | SH2B3 | rs3184504 | C | 1.09 | 0.53 | 1.0019 | 0.23% |
| 12q24.21 | TBX3 | rs59336 | T | 1.09 | 0.48 | 1.0019 | 0.23% |
| 12q24.22 | NOS1 | rs73208120 | G | 1.16 | 0.11 | 1.0021 | 0.26% |
| 14q22.2 | BMP4 | rs1957636 | T | 1.08 | 0.4 | 1.0014 | 0.18% |
| 14q22.2 | BMP4 | rs4444235 | C | 1.11 | 0.46 | 1.0027 | 0.33% |

TABLE 4-continued

SNPs associated with colorectal cancer. The table indicates the SNP
nomenclature, the gene(s) closest to or within the likely regulatory target of the SNP,
the reported risk allele genotype, the reported risk allele frequency in controls, the
reported association with colorectal cancer per risk allele (odds ratio), the familial
relative risk (FRR) attributable to the SNP, and the proportion of the log FRR due to
the SNP. *Gene/s closest to or likely regulatory target of SNP. SNPs in linkage
disequilibrium are shown in square brackets [ ].

| Locus | Gene* | SNP | Risk allele | Per risk allele OR | Freq of risk allele | FRR | Proportion of log FRR |
|---|---|---|---|---|---|---|---|
| 15q13.3 | SCG5; GREM1 | rs11632715 | A | 1.12 | 0.47 | 1.0032 | 0.39% |
| 15q13.3 | SCG5; GREM1 | rs16969681 | T | 1.18 | 0.09 | 1.0022 | 0.28% |
| 16q22.1 | CDH1 | rs9929218 | G | 1.1 | 0.71 | 1.0019 | 0.23% |
| 16q24.1 | FOXL1 | rs16941835 | C | 1.15 | 0.21 | 1.0032 | 0.40% |
| 17q21 | STAT3 | rs744166 | G | 1.27 | 0.55 | 1.0142 | 1.74% |
| 18q21.1 | SMAD7 | rs4939827 | T | 1.18 | 0.52 | 1.0069 | 0.84% |
| 19q13.11 | RHPN2 | rs10411210 | C | 1.15 | 0.9 | 1.0018 | 0.22% |
| 19q13.2 | TMEM91; TGFB1 | 19qhap^; [rs1800469, rs2241714] | G | 1.16 | 0.49 | 1.0055 | 0.68% |
| 20p12.3 | FERMT1; BMP2 | rs2423279 | C | 1.14 | 0.3 | 1.0036 | 0.44% |
| 20p12.3 | FERMT1; BMP2 | rs4813802 | G | 1.09 | 0.36 | 1.0017 | 0.21% |
| 20p12.3 | FERMT1; BMP2 | rs961253 | A | 1.12 | 0.36 | 1.003 | 0.36% |
| 20q13.1 | PREX1 | rs6066825 | A | 1.09 | 0.64 | 1.0017 | 0.21% |
| 20q13.33 | LAMA5 | rs4925386 | C | 1.08 | 0.68 | 1.0013 | 0.16% |

Example 2—Risk Allele Simulation

A simulation to determine the ability of the cumulative number of risk alleles of the SNPs to discriminate cases of colorectal cancer from controls and to estimate the risk of colorectal cancer as a function of the number of risk alleles was conducted using the software PLINK (Purcell et al., 2007) (pngu.mgh.harvard.edu/purcell/plink/).

A population of 1,000,000 people with colorectal cancer (cases) and 1,000,000 people without colorectal cancer (controls) was simulated. The distribution of SNP risk alleles for the simulated population was matched to the reported risk allele frequencies and per allele odds ratios of colorectal cancer associations. A simplistic model of risk where the association with colorectal cancer for each SNP was independent was assumed in this assessment. In this analysis it was also assumed that the odds ratios reported for colorectal cancer for each SNP were applicable to both men and women and were constant with age.

The discriminatory power of the SNPs was assessed to distinguish cases from controls using a receiver operating curve and estimating the area under the curve (the probability that a randomly selected colorectal cancer case will have more risk alleles than a randomly selected control). The odds ratios was estimated for colorectal cancer risk for: (i) being in the highest and lowest quintile for the number of risk alleles being in the middle quintile; (ii) being in the highest and lowest decile for the number of risk alleles versus being in the median number of risk alleles; and (iii) per standard deviation of risk alleles. Cut-offs for number of risk alleles for quintiles and deciles, and the standard deviation, were based on the distribution of risk alleles for the controls.

Under the assumption that these odds ratios were constant with age and equal for men and women, the cumulative lifetime risk (from birth to age 70 years) and the five-year risk for each age category of colorectal cancer was estimated for Australia and the USA by the number of SNP risk alleles. The age-specific Australian and USA population incidences were assumed to be the incidences for those with the median number of risk alleles. Colorectal cancer population incidences were obtained from the Australian Institute of Health and Welfare, 2015 and the Surveillance, Epidemiology, and End Results (SEER) Program Cancer Statistics (Howlander et al., 1975-2011).

The proportion of log familial relative risk (FRR; the odds ratio for colorectal cancer associated with having a first-degree relative with colorectal cancer) that could be attributable to the risk alleles of the SNPs was estimated. The Hardy-Weinberg equilibrium for each SNP, linkage equilibrium between the SNPs, and a multiplicative model for the associations of the SNPs with colorectal cancer risk was assumed. More precisely, let $SNP_1, \ldots, SNP_{45}$ be the known colorectal cancer-associated SNPs and let clinical factor$_1$, . . . , clinical factor$_m$ be unknown ones (note: these could be any heritable factors contributing to the FRR, but for simplicity we think of them as SNPs). Then if $G_L$ is a random variable giving the number of risk alleles at $SNP_i$ for a random person from the population, then $G_1, \ldots, G_m$ are all independent random variables (by linkage equilibrium) and the log-odds ratio for a random person is $X_1 + \ldots + X_m$ (by the assumed multiplicative model), where $X_i = G_i \log OR_i$ and $OR_i$ is the per-allele odds ratio for $SNP_i$. A formula of Antoniou et al. (2003) derived rigorously in Win et al. (2014) then becomes $\log FRR = \frac{1}{2}[Var(X_1) + \ldots + Var(X_m)]$.

This shows that the log FRR is the sum of independent components from the known and unknown colorectal cancer-associated SNPs. The proportion of the log FRR due to the known SNPs is $\frac{1}{2}(Var(X_1) + \ldots + Var(X_{45}))/\log FRR$ while the proportion due to the unknown SNPs is one minus this value. It was assumed that the FRR of having at least one first-degree relative with colorectal cancer was 2.25, based on a previous meta-analysis of family history of colorectal cancer (Johns et al., 2001) and an elementary calculation (assuming Hardy-Weinberg equilibrium) shows that $Var(X_1) = 2p_i(1-p_i)(\log OR_i)^2$, where $p_i$ is the minor allele frequency of $SNP_i$. Using this statistic, the five-year risk of colorectal cancer by the number of risk alleles was estimated, with and without a family history of colorectal cancer.

The number of risk alleles for the simulated people with and without colorectal cancer are shown in FIG. 1 and can be summarized as follows:

Those with colorectal cancer: median 42 risk alleles, range 21 to 61 risk alleles, mean 41.6 risk alleles, standard deviation 4.2 risk alleles;

Those without colorectal cancer: median 40 risk alleles, range 20 to 59, mean 39.7 risk alleles, standard deviation 4.2 risk alleles; upper quartile 44 or more risk alleles; lower quartile 36 or fewer risk alleles; upper decile 46 or more risk alleles; lower decile 34 or fewer risk alleles) (FIG. 1).

Having 29 risk alleles corresponded to a lifetime risk of colorectal cancer of 1.4% for a person from Australia and 1.0% for a person from the USA. The respective risks for 36 risk alleles were 2.9% and 2.0%; for 43 risk alleles were 6.1% and 4.3%; and for 50 risk alleles were 12.5% and 8.8% (FIG. 1). Compared with people in the middle quintile for the number of risk alleles, the odds ratio for colorectal cancer was 1.81 for people in the highest quintile of number of risk alleles, and 0.51 for people in the lowest quintile; this is equivalent to a 3.55-fold inter-quintile risk (highest vs. lowest quintile). Compared with people with the median of 40 risk alleles, the odds ratio for colorectal cancer was 2.27 for people in the highest decile of the number of risk alleles, and 0.45 for people in the lowest decile; this is equivalent to a 5.04-fold inter-decile risk (highest vs. lowest decile). The odds ratio per standard deviation of risk alleles was 1.57. The receiver operating characteristic curve had an area under the curve of 0.63.

Based on the 2011 population incidence rates for colorectal cancer in Australia, the average cumulative risk of colorectal cancer to age 70 years was 3.3%. For people in the highest quintile for number of risk alleles, the cumulative risk was 5.9% (11.5% if they also had a first-degree relative with colorectal cancer, and 5.5% if they did not) compared with 1.7% for people in the lowest quintile for number of risk alleles (3.2% if they also had a first-degree relative with colorectal cancer, and 1.6% if they did not).

For people in the highest decile for number of risk alleles, the cumulative risk was 7.4% (13.4% if they also had a first-degree relative with colorectal cancer, and 6.9% if they did not) compared with 1.5% for people in the lowest decile for number of risk alleles (2.8% if they also had a first-degree relative with colorectal cancer, and 1.4% if they did not; FIG. 2 A, B). The estimates for males were on average approximately 13% higher and for females the estimates were on average 16% lower than for males and females combined (FIGS. 4 and 5).

The 5-year risk of colorectal cancer for the average (previously unaffected) person in Australia reaches 1% at age 63 years. The same 1% 5-year risk is attained approximately 7 years earlier for people in the highest quintile for number of risk alleles (and approximately 14 years earlier if they also had a family history of colorectal cancer), and approximately 10 years earlier for people in the highest decile for number of risk alleles (16 years earlier if they also had a family history; FIG. 2 Panels C, D and Table 5). On average males reached the 1% risk threshold 1-2 years earlier, and females reached the threshold on average 3-4 years later than for males and females combined (Table 5).

TABLE 5

Age (years) at which the 5-year risk of colorectal cancer reaches or exceeds thresholds of 1%, for various categories of family history of colorectal cancer (at least one first-degree relative) and risk alleles of 45 SNPs.

| Risk category | USA | | | Australia | | |
| --- | --- | --- | --- | --- | --- | --- |
| | All | male | female | All | male | female |
| General population | 70 | 67 | 73 | 63 | 61 | 71 |
| Family history (1st degree relative) | 58 | 55 | 61 | 53 | 52 | 59 |
| Highest quintile of risk alleles | 61 | 57 | 62 | 56 | 55 | 62 |
| Highest decile of risk alleles | 58 | 53 | 59 | 53 | 52 | 59 |
| Family history and highest quintile | 50 | 48 | 52 | 49 | 48 | 55 |
| Family history and highest decile | 48 | 46 | 48 | 47 | 46 | 53 |
| Family history and lowest quintile | 71 | 66 | 73 | 63 | 61 | 72 |
| Family history and lowest decile | 74 | 73 | 80 | 65 | 63 | 76 |

Given that the population incidence rates of colorectal cancer in the USA are lower (particularly after age 50 years compared with Australia), the associated risks based on the number of risk alleles and family history are also lower than those for Australia (FIG. 3 Panels A, B, FIGS. 6 and 7). In comparison, the same 1% risk is attained approximately 9 years earlier for people in the highest quintile for number of risk alleles (20 years earlier if they also had a family history of colorectal cancer), and approximately 12 years earlier for people in the highest decile for number of risk alleles (22 years earlier if they also had a family history; FIG. 3 Panels C, D and Table 5). On average males reached the 1% risk threshold 3-5 years earlier, and females reached the threshold on average 1-3 years later than for males and females combined (Table 5).

Example 3—Categorising Subjects by Risk of Colorectal Cancer

Simulations were used to quantify the utility of a panel of 45 risk-associated SNPs to categorize people based on their risk of colorectal cancer. People at the ends of the spectrum for risk alleles were considerably more likely to develop colorectal cancer (high end) or less likely to develop colorectal cancer (low end). Because the total variation in risk associated with these SNPs across the population can explain about one quarter of the total FRR, the predictive strength of the SNP profile is increased if family history of colorectal cancer is also taken into account. Given that the strength of association with colorectal cancer for those in the lowest 20% of the population (for number of risk alleles of these SNPs) is roughly the inverse of the increased risk associated with the remaining FRR, people who have a family history of colorectal cancer but who also are in the lowest quintile of the population for number of risk alleles of these SNPs, are at population risk.

Thus, measurement of these SNPs is a useful method for assessment of colorectal cancer risk, and can be used as a tool for determining who should be recommended for colorectal cancer screening, and at what intensity. For example, a person in the top 20% of the population for risk alleles (at least 44 alleles) reaches the average population 5-year risk 9 years earlier than the average person. Therefore, if the average person meets the risk-threshold for fecal occult blood test screening (which most national screening programs recommend) at age 50 years, then a person with at least 44 risk alleles reaches the same risk-threshold at age 41 years. The ages to begin colonoscopy screening for people with a first-degree relative with colorectal cancer would be 49 and 47 years for the highest quintile and the highest decile of risk alleles respectively. In the USA, where the population risk of colorectal cancer is lower than for Australia, the 2% threshold for being in the top quintile or decile and having a family history of colorectal cancer is reached at ages 62 and 59 years respectively.

Example 4—Risk Prediction for Non-Lynch Syndrome Colorectal Cancer Based on 45 Independent Risk-Associated SNPs and Multi-Generational Family History A family history-based risk score that gives a log transformed age-adjusted 5-year colorectal cancer risk based on multi-generational colorectal cancer data using a mixed major gene—polygenic model (CRiPT) was determined. This clinical risk assessment was combined with the risk score based of the 45 SNPs listed in Table 4. The inventors used logistic regression to estimate the odds ratio per adjusted standard deviation (OPERA) (Dite et al., 2016) for each score with colorectal cancer risk.

The SNP-based score, the family history-based score, and the combined SNP and family history-based scores all associated with colorectal cancer risk with OPERAs of 1.40 (95% confidence interval [CI], 1.24-1.58), 1.39 (1.26-1.53), and 1.59 (1.42-1.79), respectively. These are equivalent to inter-quartile risk ratios (risk in highest 25% of the population for the risk score divided by the risk in the lowest 25% of the population) of 2.4, 2.3 and 3.2. The combined risk score gave better fits than the SNP- and family history-based scores (both P<0.001). For people with a moderately strong family history that puts them at about 4-fold increased risk (similar to having two first degree relatives diagnosed with colorectal cancer over age 50 years), these estimates predict that those in the top quartile (25%) for SNP scores at more than 6-times the population risk, while those in the bottom quartile are at less than 2.5-times population risk.

Thus, combining information on SNPs with multi-generational family history improved the ability to prediction colorectal cancer by approximately 40%. Therefore, given that it might reclassify clinical management for about one-half of these people, this new combined risk measure can be used to inform better targeted colorectal cancer screening based on risk.

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

The present application claims priority from AU 2016900254 filed 28 Jan. 2016 and 2016903246 filed 16 Aug. 2016, the disclosures of which are incorporated herein by reference.

All publications discussed above are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

REFERENCES

Ait Ouakrim et al. (2012) Cancer Prev Res. (Phila) 5:240-247.
Antoniou et al. (2003) Genet Epidemiol. 25:190-202.
Ausubel et al. (editors) (1998), Current Protocols in Molecular Biology, Greene Pub. Associates and Wiley-Interscience (including all updates until present).
Brenner et al. (2014) BMJ 348 g2467.
Brown (editor) (1991), Essential Molecular Biology: A Practical Approach, Volumes 1 and 2, IRL Press.
Coligan et al. (editors) Current Protocols in Immunology, John Wiley & Sons (including all updates until present).
Devlin and Risch (1995) Genomics. 29: 311-322.
Dite et al. (2016) Cancer Epidemiol Biomarkers Prev 25:359-365.
Glover and Hames (editors) (1995 and 1996) DNA Cloning: A Practical Approach, Volumes 1-4, IRL Press.
Harlow and Lane (editors) (1988) Antibodies: A Laboratory Manual, Cold Spring Harbour Laboratory.
Hartl (1981) A Primer of Population Genetics Washington University, Saint Louis Sinauer Associates, Inc. Sunderland, Mass. ISBN: 0-087893-271-2.
Hewitson et al. (2007) The Cochrane database of systematic reviews doi:10.1002/14651858.CD001216.pub2(1), CD001216.
Johns et al (2001) Gastroenterol. 96:2992-3003.
Lynch and Walsh (1998) Genetics and Analysis of Quantitative Traits, Sinauer Associates, Inc. Sunderland Mass. ISBN 0-87893-481-2.
Mavaddat et al. (2015) J Natl Cancer Inst 107:djv036.
Pencina et al. (2008) Statistics in Medicine 27: 157-172.
Perbal (2000) A Practical Guide to Molecular Cloning, John Wiley and Sons (1984)
Purcell et al. (2007) Am J Hum Genet. 81:559-575.
Purcell et al. (2007) (pngu.mgh.harvard.edu/purcell/plink/).
Sambrook et al. (1989) Molecular Cloning: A Laboratory Manual, Cold Spring Harbour Laboratory Press.
Slatkin and Excoffier (1996) Heredity 76: 377-383.
Spain et al. (2012) Hum Mol Genet. 21:934-946.
Tijssen (1993) Laboratory Techniques in Biochemistry and Molecular Biology-Hybridization with Nucleic Acid Probes Elsevier, New York.
Usher-Smith et al. (2015) Cancer Prev Res 9: 13-26.
Win et al. (2014) Gastroenterology 146:1208-1211, e1201-1205.

The invention claimed is:

1. A method of prophylactically treating a human subject determined to have an increased risk for colorectal cancer, the method comprising:
(i) determining a risk score for the human subject of developing colorectal cancer by the following steps:
a) obtaining the odds ratio (OR) of association with colorectal cancer of 45 single nucleotide polymorphisms (SNPs) consisting of SNPs rs72647484, rs10911251, one of rs6687758 or rs6691170, rs11903757, rs812481, rs35360328, rs10936599, rs3987, rs35509282, rs647161, rs1321311, rs16892766, one of rs6983267 or rs10505477 or rs7014346, rs719725, rs10904849, rs10795668, rs704017, one of rs11190164 or rs1035209, rs12241008, one of rs174537 or rs4246215 or rs174550 or rs1535, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, one of rs1800469 or rs2241714, rs2423279, rs4813802, rs961253, rs6066825, and rs4925386;
b) obtaining the identity of alleles present in the genome of a human subject at a panel of SNPs consisting of the 45 SNPs;
c) determining an adjusted risk score for each of the 45 SNPs of the human subject, where:

(i) if two major alleles are present at the SNP, then the adjusted risk score for the SNP is $1/\mu$,
(ii) if one major and one minor allele are present at the SNP, then the adjusted risk score for the SNP is $OR/\mu$,
(iii) if two minor alleles are present at the SNP, then the adjusted risk score for the SNP is $OR^2/\mu$, and
(iv) if the genotype is missing for the SNP, then the adjusted risk score for the SNP is 1,
where $\mu=(1-p)^2+2p(1-p)OR+p^2OR^2$, wherein OR is the odds ratio of a minor allele at the given SNP and p is the frequency of the minor allele;
d) multiplying together the adjusted risk score for each of the 45 SNPs of the human subject to produce a genetic risk score of the human subject;
e) obtaining a clinical risk assessment of the human subject;
f) combining the clinical risk assessment of the human subject with the genetic risk score of the human subject; and
g) producing a number which represents the risk of the human subject developing colorectal cancer relative to the average risk of developing colorectal cancer in the population to which the human subject belongs;
(ii) identifying the human subject as at increased risk for colorectal cancer based on the risk score; and
(iii) prophylactically treating the human subject with a nonsteroidal anti-inflammatory drug.

2. The method of claim 1, wherein the clinical risk assessment involves obtaining information from the subject on one or more of the following: medical history of colorectal cancer, age, family history of colorectal cancer, results of previous colonoscopy or sigmoidoscopy screening and race/ethnicity.

3. The method of claim 1, wherein the clinical risk assessment involves obtaining information from the subject on age and/or first degree relatives' history of colorectal cancer.

4. The method of claim 1, wherein the subject has had a positive fecal occult blood test.

5. The method of claim 1, wherein the 45 SNPs are rs72647484, rs10911251, rs6687758, rs11903757, rs812481, rs35360328, rs10936599, rs3987, rs35509282, rs647161, rs1321311, rs16892766, rs6983267, rs719725, rs10904849, rs10795668, rs704017, rs11190164, rs12241008, rs174537, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, rs1800469, rs2423279, rs4813802, rs961253, rs6066825, and rs4925386.

6. The method of claim 1, wherein the nonsteroidal anti-inflammatory drug is aspirin.

7. A method of prophylactically treating a human subject determined to have an increased risk for colorectal cancer, the method comprising:
(i) determining a risk score for the human subject of developing colorectal cancer by the following steps:
a) obtaining the odds ratio (OR) of association with colorectal cancer of 45 single nucleotide polymorphisms (SNPs) consisting of SNPs rs72647484, rs10911251, one of rs6687758 or rs6691170, rs11903757, rs812481, rs35360328, rs10936599, rs3987, rs35509282, rs647161, rs1321311, rs16892766, one of rs6983267 or rs10505477 or rs7014346, rs719725, rs10904849, rs10795668, rs704017, one of rs11190164 or rs1035209, rs12241008, one of rs174537 or rs4246215 or rs174550 or rs1535, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, one of rs1800469 or rs2241714, rs2423279, rs4813802, rs961253, rs6066825, and rs4925386;
b) obtaining the identity of alleles present in the genome of a human subject at a panel of SNPs consisting of the 45 SNPs;
c) determining an adjusted risk score for each of the 45 SNPs of the human subject, where:
(i) if two major alleles are present at the SNP, then the adjusted risk score for the SNP is $1/\mu$,
(ii) if one major and one minor allele are present at the SNP, then the adjusted risk score for the SNP is $OR/\mu$,
(iii) if two minor alleles are present at the SNP, then the adjusted risk score for the SNP is $OR^2/\mu$, and
(iv) if the genotype is missing for the SNP, then the adjusted risk score for the SNP is 1,
where $\mu=(1-p)^2+2p(1-p)OR+p^2OR^2$, wherein OR is the odds ratio of a minor allele at the given SNP and p is the frequency of the minor allele;
d) multiplying together the adjusted risk score for each of the 45 SNPs of the human subject to produce a genetic risk score of the human subject;
e) obtaining a clinical risk assessment of the human subject;
f) combining the clinical risk assessment of the human subject with the genetic risk score of the human subject; and
g) producing a number which represents the risk of the human subject developing colorectal cancer relative to the average risk of developing colorectal cancer in the population to which the human subject belongs;
(ii) identifying the human subject as at increased risk for colorectal cancer based on the risk score; and
(iii) prophylactically treating the human subject with hormone therapy.

8. The method of claim 7, wherein the clinical risk assessment involves obtaining information from the subject on one or more of the following: medical history of colorectal cancer, age, family history of colorectal cancer, results of previous colonoscopy or sigmoidoscopy screening and race/ethnicity.

9. The method of claim 7, wherein the clinical risk assessment involves obtaining information from the subject on age and/or first degree relatives' history of colorectal cancer.

10. The method of claim 7, wherein the subject has had a positive fecal occult blood test.

11. The method of claim 7, wherein the 45 SNPs are rs72647484, rs10911251, rs6687758, rs11903757, rs812481, rs35360328, rs10936599, rs3987, rs35509282, rs647161, rs1321311, rs16892766, rs6983267, rs719725, rs10904849, rs10795668, rs704017, rs11190164, rs12241008, rs174537, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, rs1800469, rs2423279, rs4813802, rs961253, rs6066825, and rs4925386.

12. A method of prophylactically treating a human subject determined to have an increased risk for colorectal cancer, the method comprising:
(i) determining a risk score for the human subject of developing colorectal cancer by the following steps:
a) obtaining the odds ratio (OR) of association with colorectal cancer of 45 single nucleotide polymorphisms (SNPs) consisting of SNPs rs72647484, rs10911251, one of rs6687758 or rs6691170, rs11903757, rs812481, rs35360328, rs10936599, rs3987, rs35509282, rs647161, rs1321311, rs16892766, one of rs6983267 or rs10505477 or rs7014346, rs719725, rs10904849, rs10795668, rs704017, one of rs11190164 or rs1035209, rs12241008, one of rs174537 or rs4246215 or rs174550 or rs1535, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, one of rs1800469 or rs2241714, rs2423279, rs4813802, rs961253, rs6066825, and rs4925386;
b) obtaining the identity of alleles present in the genome of a human subject at a panel of SNPs consisting of the 45 SNPs;
c) determining an adjusted risk score for each of the 45 SNPs of the human subject, where:
(i) if two major alleles are present at the SNP, then the adjusted risk score for the SNP is $1/\mu$,
(ii) if one major and one minor allele are present at the SNP, then the adjusted risk score for the SNP is $OR/\mu$,
(iii) if two minor alleles are present at the SNP, then the adjusted risk score for the SNP is $OR^2/\mu$, and
(iv) if the genotype is missing for the SNP, then the adjusted risk score for the SNP is 1,
where $\mu=(1-p)^2+2p(1-p)OR+p^2OR^2$, wherein OR is the odds ratio of a minor allele at the given SNP and p is the frequency of the minor allele;
d) multiplying together the adjusted risk score for each of the 45 SNPs of the human subject to produce a genetic risk score of the human subject;
e) obtaining a clinical risk assessment of the human subject;
f) combining the clinical risk assessment of the human subject with the genetic risk score of the human subject; and
g) producing a number which represents the risk of the human subject developing colorectal cancer relative to the average risk of developing colorectal cancer in the population to which the human subject belongs;
(ii) identifying the human subject as at increased risk for colorectal cancer based on the risk score; and
(iii) prophylactically treating the human subject by increasing fiber, mono-saturated fatty acids and/or fish oil in the human subject's diet.

13. The method of claim 12, wherein the clinical risk assessment involves obtaining information from the subject on one or more of the following: medical history of colorectal cancer, age, family history of colorectal cancer, results of previous colonoscopy or sigmoidoscopy screening and race/ethnicity.

14. The method of claim 12, wherein the clinical risk assessment involves obtaining information from the subject on age and/or first degree relatives' history of colorectal cancer.

15. The method of claim 12, wherein the subject has had a positive fecal occult blood test.

16. The method of claim 12, wherein the 45 SNPs are rs72647484, rs10911251, rs6687758, rs11903757, rs812481, rs35360328, rs10936599, rs3987, rs35509282, rs647161, rs1321311, rs16892766, rs6983267, rs719725, rs10904849, rs10795668, rs704017, rs11190164, rs12241008, rs174537, rs3824999, rs3802842, rs3217810, rs3217901, rs10774214, rs11169552, rs7136702, rs3184504, rs59336, rs73208120, rs1957636, rs4444235, rs11632715, rs16969681, rs9929218, rs16941835, rs744166, rs4939827, rs10411210, rs1800469, rs2423279, rs4813802, rs961253, rs6066825, and rs4925386.

* * * * *